US009644223B2

(12) United States Patent
Yamaguchi et al.

(10) Patent No.: US 9,644,223 B2
(45) Date of Patent: May 9, 2017

(54) HYPERTHERMOSTABLE ENDOGLUCANASE BELONGING TO GH FAMILY 12

(71) Applicant: HONDA MOTOR CO., LTD., Minato-Ku, Tokyo (JP)

(72) Inventors: Asuka Yamaguchi, Wako (JP); Jiro Okuma, Wako (JP); Yoshitsugu Hirose, Wako (JP); Migiwa Suda, Wako (JP); Yasuhiro Kondo, Wako (JP); Tomohiko Kato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 21 days.

(21) Appl. No.: 14/816,603

(22) Filed: Aug. 3, 2015

(65) Prior Publication Data

US 2016/0122791 A1    May 5, 2016

(30) Foreign Application Priority Data

Aug. 4, 2014  (JP) ................................. 2014-158655

(51) Int. Cl.
| | | |
|---|---|---|
| *C12P 19/14* | (2006.01) | |
| *C12N 9/42* | (2006.01) | |
| *C12P 19/02* | (2006.01) | |

(52) U.S. Cl.
CPC ............ *C12P 19/14* (2013.01); *C12N 9/2437* (2013.01); *C12P 19/02* (2013.01); *C12Y 302/01004* (2013.01)

(58) Field of Classification Search
CPC .................. C12N 9/2437; C12N 9/248; C12Y 302/01004; C12Y 302/01008; C12P 19/14
See application file for complete search history.

(56) References Cited

U.S. PATENT DOCUMENTS

| | | | |
|---|---|---|---|
| 6,022,725 A * | 2/2000 | Fowler | ............... C11D 3/38645 435/209 |
| 6,190,890 B1 | 2/2001 | Van Den Broeck et al. | |
| 6,812,018 B2 | 11/2004 | Wicher et al. | |
| 7,041,488 B2 | 5/2006 | Outtrup et al. | |
| 7,049,125 B2 | 5/2006 | Dunn-Coleman et al. | |
| 2003/0129723 A1 * | 7/2003 | Ishikawa | .......... C12Y 302/0100 435/200 |

FOREIGN PATENT DOCUMENTS

| | | | |
|---|---|---|---|
| JP | 2003-210182 A | 7/2003 | |
| JP | 2007-529993 A | 11/2007 | |
| WO | 97/44361 A1 | 11/1997 | |
| WO | 2005/003319 A2 | 1/2005 | |
| WO | 2012/015605 A1 | 2/2012 | |

OTHER PUBLICATIONS

Extended European search report, with a mailing date of Nov. 6, 2015 issued in the corresponding EP Patent Application 15179535.8.
Database UniProt [Online], "SubName: Full=Glycoside hydrolase family 12, {ECO:00003313 EMBL:ADM28608.1};", retrieved from EBI accession No. UNIPROT:E0SSM3, Database accession No. E0SSM3, Nov. 2, 2010.
Database Geneseq [Online], "Caldivirga maquilingensis endo-beta-1, 4-glucanase encoding gene, SEQ: 1.", retrieved from EBI accession No. GSN:AZI78800, Database accession No. AZI78800, Jul. 21, 2011.
Petre et al., "Purification and properties of the endoglucanase C of Clostridium thermocellum produced in *Escherichia coli*", Biochimie, vol. 68, Jan. 1, 1986, [retrieved on Aug. 28, 2015], pp. 687-695.
Yeoman et al., "Thermostable enzymes as biocatalysts in the biofuel industry", Advances in Applied Microbiology, Academic Press, US, vol. 70, Jan. 1, 2010, pp. 1-55, [retieved on Mar. 6, 2010].
Moloney et al., "Isolation and characterization of the 1,4-Beta-D-glucan glucanohydrolases of Talaromyces emersonii", Biochemical Journal, 1985, vol. 225, pp. 365-374.
Penttila et al., Gene, An International Journal Focusing on Gene Cloning and Gene Structure and Function, 1986, vol. 45, No. 2, p. 253-263.
Petre et al., "Purification and Properties of the endoglucanase C of Costridium Thermocellum Produced in *Escherichia coli*", Biochimie, May 1986, vol. 68, No. 5, pp. 687-695.
Chhabra et al., "Regulation of Endo-Acting Glycosyl Hydrolases in the Hyperthermophilic Bacterium Thermotoga maritima Grown on Glucan- and Mannan-Based Polysaccharides", Applied and Environmental Microbiology, 2002, vol. 68, No. 2, p. 545-554.
Nurachman et al., "Cloning of the Endoglucanase Gene from a Bacillus amyloliquefaciens PSM 3.1 in *Escherichia coli* Revealed Catalytic Triad Residues Thr-His-Glu" American Journal of Biochemistry and Biotechnology, 2010, vol. 6, p. 268-274.
Huang et al., "A Highly acid-stable and thermostable endo-Beta-glucanase from the thermoacidophilic archaeon Sulfolobus solfataricus", Biochemical Journal, 2005, vol. 385, 581-588.

(Continued)

*Primary Examiner* — Kagnew H Gebreyesus
(74) *Attorney, Agent, or Firm* — Carrier Blackman & Associates, P.C.; Joseph P. Carrier; Fulchand P. Shende

(57) ABSTRACT

A hyperthermostable endoglucanase including an endoglucanase catalytic domain, the endoglucanase catalytic domain including:
(A) a polypeptide including an amino acid sequence represented by SEQ ID NO: 1;
(B) a polypeptide including an amino acid sequence in which at least one amino acid is deleted, substituted, or added in the amino acid sequence represented by SEQ ID NO: 1, and having hydrolytic activity using p-nitrophenyl-β-D-cellobioside as a substrate at least under conditions of a temperature of 100° C. and a pH of 5.5; or
(C) a polypeptide including an amino acid sequence having at least 70% sequence identity with the amino acid sequence represented by SEQ ID NO: 1, and having hydrolytic activity using p-nitrophenyl-β-D-cellobioside as a substrate at least under conditions of a temperature of 100° C. and a pH of 5.5.

16 Claims, 5 Drawing Sheets

(56) References Cited

OTHER PUBLICATIONS

Liebl et al., "Analysis of a Thermotoga maritima DNA fragment encoding two similar thermostable cellulases, CelA and CelB, and characterization of the recombinant enzymes", Microbiology, 1996, vol. 142, 2533-2542.

Noguchi et al., "MetaGeneAnnotator: Detecting Species-Specific Patterns of Ribosomal Binding Site for Precise Gene Prediction in Anonymous Prokaryotic and Phage Genomes", DNA Research, 2008, 15(6), pp. 387-396.

Finn et al., "The Pham protein families database", Nucleic Acids Research Database, 2010, vol. 38, p. D211-222.

Durbin et al., 'The theory behind profile HMMs. Biological sequence analysis: probabilistic models of proteins and nucleic acids', 1998, Cambridge University Press.

Database UniProt [Online], "SubName: Full=Glycoside hydrolase family 12, {ECO:0000313 EMBL:ADM28608.1};", retrieved from EBI accession No. UNIPROT:E0SSM3, Database accession No. E0SSM3, Nov. 2, 2010.

* cited by examiner

FIG. 1

HYPERTHERMOSTABLE ENDOGLUCANASE BELONGING TO GH FAMILY 12

TECHNICAL FIELD

The present invention relates to a hyperthermostable endoglucanase, a polynucleotide that encodes the aforementioned hyperthermostable endoglucanase, an expression vector for expressing the aforementioned hyperthermostable endoglucanase, a transformant incorporated with the aforementioned expression vector, and a method for producing a lignocellulose degradation product using the aforementioned hyperthermostable endoglucanase.

Priority is claimed on Japanese Patent Application No. 2014-158655, filed Aug. 4, 2014, the content of which is incorporated herein by reference.

BACKGROUND ART

In recent years, the development of alternative energy to oil is a very important issue, because of environmental problems, such as global warming and aerial pollution, in addition to the concern related to transportation energy supply. Plant biomass is the most abundant renewable energy source on earth, which is expected to serve as an alternative source to petroleum. The main components of plant biomass (lignocellulose) are polysaccharides such as celluloses and hemicelluloses (including xylan, arabinan and mannan), lignin and other pectins. These polysaccharides are hydrolyzed into monosaccharides such as glucose and xylose by a variety of glycoside hydrolases, and are used as a biofuel or a raw material of chemical products.

Lignocellulose having a complex structure is persistent, and is difficult to degrade or hydrolyze with a single enzyme. For this reason, the hydrolysis of cellulose among the polysaccharides generally requires three types of enzymes: an endoglucanase (endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21) that are glycoside hydrolases. On the other hand, hemicelluloses include xylan, arabinan, mannan and the like, and although the composition thereof depends on the type of the plants, for example, xylan is a major constituent in broad-leaved trees, herbaceous plants and the like. For the hydrolysis of xylan, it is thought that xylanase (endo-1,4-β-xylanase, EC 3.2.1.8) and β-xylosidase (EC 3.2.1.37) are required.

In the conventional lignocellulose to ethanol conversion process, high-solid loading up to 30-60% in initial substrate concentration has been attempted for the purpose of higher energy efficiency and less water usage. The enzymatic hydrolysis of lignocellulose by such high-solid loading processes results in the high viscosity of the hydrolyzed biomass solution so that the hydrolysis of lignocellulose hardly proceeds. Therefore, for example, by carrying out the enzymatic hydrolysis process at a high temperature of 80° C. or higher using a thermostable enzyme, in addition to an increase in the hydrolysis reaction rate, since the viscosity of the hydrolyzed biomass solution also reduces, the shortening of the hydrolysis reaction time and the reduction of the amount of enzyme are expected to be achieved. For this reason, for various glycoside hydrolases, development of enzymes that are more excellent in terms of thermostability has been desired.

Many thermostable glycoside hydrolases have been obtained by isolating and identifying the thermophilic microorganisms that live in a high temperature environment, cloning the genes from these cultured and isolated microorganisms and determining the DNA sequence thereof, followed by the expression thereof using *Escherichia coli*, filamentous fungi and the like. Numerous endoglucanases that can be used for hydrolysis of lignocellulose have been isolated from fungi, bacteria, and the like, and some of them are commercially available as reagents (for example, see Patent Documents 1 to 4 and Non-Patent Documents 1 to 5). However, many of them are endoglucanases having optimum temperatures within middle to high temperature ranges from 40° C. to 80° C., and few enzymes are capable of maintaining activity for a prolonged period of time in an ultra-high temperature range of 80° C. or higher. As the hyperthermostable endoglucanases having optimum temperatures of 80° C. or higher, endoglucanases derived from archaea (Patent Document 5, Non-patent Document 6), endoglucanases derived from bacteria (Patent Document 6, Non-Patent Document 7) and the like have been reported to date. However, the degradation characteristics for various substrate differ, and there is also a report describing the changes in the optimum temperature in a substrate-dependent manner. In addition, the thermal stability (in terms of the half-life of the enzyme activity) within an ultra-high temperature range is generally about 2 to 3 hours, which is not so high.

PRIOR ART DOCUMENTS

Patent Documents

[Patent Document 1] U.S. Pat. No. 6,190,890
[Patent Document 2] U.S. Pat. No. 7,049,125
[Patent Document 3] U.S. Pat. No. 7,041,488
[Patent Document 4] Published Japanese Translation No. 2007-529993 of the PCT International Publication
[Patent Document 5] Japanese Unexamined Patent Application, First Publication No. 2003-210182
[Patent Document 6] U.S. Pat. No. 6,812,018

Non-Patent Documents

[Non-Patent Document 1] Moloney et al., Biochemical Journal, 1985, vol. 225, p. 365-374.
[Non-Patent Document 2] Penttila et al., Gene, 1986, vol. 45, p. 253-263.
[Non-Patent Document 3] Petre et al., Biochhnie, 1986, vol. 68, p 687-695.
[Non-Patent Document 4] Chhabra et al., Applied and Environmental Microbiology, 2002, vol. 68, p. 545-554.
[Non-Patent Document 5] Nurachman et al., American Journal of Biochemistry and Biotechnology, 2010, vol. 6, p. 268-274.
[Non-Patent Document 6] Huang et al., Biochimie Journal, 2005, vol. 385, 581-588.
[Non-Patent Document 7] Liebl et al., Microbiology, 1996, vol. 142, 2533-2542.

SUMMARY OF THE INVENTION

Problems to be Solved by the Invention

It is an object of the present invention to provide a novel hyperthermostable endoglucanase which exhibits hydrolytic activity using p-nitrophenyl-β-D-cellobioside (PNPC) as a substrate at least under conditions of a temperature of 100° C. and a pH of 5.5, a polynucleotide that encodes the aforementioned hyperthermostable endoglucanase, an expression vector for expressing the aforementioned hyperthermostable endoglucanase, a transformant incorporated with the aforementioned expression vector, and a method for producing a lignocellulose degradation product using the aforementioned hyperthermostable endoglucanase.

Means for Solving the Problem

In order to solve the above-mentioned problems, the inventors of the present invention have successfully obtained hyperthermostable endoglucanases having novel amino acid sequences by extracting DNA directly from hot spring high temperature soils and conducting large-scale metagenome sequencing of hardly culturable microbiota. This has led to the completion of the present invention.

That is, as a hyperthermostable endoglucanase, a polynucleotide, an expression vector, a transformant, a method for producing a hyperthermostable endoglucanase, a glycoside hydrolase mixture and a method for producing a lignocellulose degradation product according to the present invention, the following aspects [1] to [10] can be mentioned.

[1] A hyperthermostable endoglucanase including an endoglucanase catalytic domain, the endoglucanase catalytic domain including: (A) a polypeptide including an amino acid sequence represented by SEQ ID NO: 1;
(B) a polypeptide including an amino acid sequence in which at least one amino acid is deleted, substituted, or added in the amino acid sequence represented by SEQ ID NO: 1, and having hydrolytic activity using p-nitrophenyl-β-D-cellobioside as a substrate at least under conditions of a temperature of 100° C. and a pH of 5.5; or
(C) a polypeptide including an amino acid sequence having at least 70% sequence identity with the amino acid sequence represented by SEQ ID NO: 1, and having hydrolytic activity using p-nitrophenyl-β-D-cellobioside as a substrate at least under conditions of a temperature of 100° C. and a pH of 5.5.

[2] The hyperthermostable endoglucanase according to the aforementioned aspect [1], which includes an endoglucanase catalytic domain including the aforementioned polypeptide of (A), uses p-nitrophenyl-β-D-cellobioside as a substrate, and may also use at least one selected from the group consisting of β-glucan, lichenan, carboxymethyl cellulose, and phosphoric acid swollen Avicel as a substrate; or which includes an endoglucanase catalytic domain including the aforementioned polypeptide of (B) or (C), and may also use at least one selected from the group consisting of β-glucan, lichenan, carboxymethyl cellulose, and phosphoric acid swollen Avicel as a substrate.

[3] A polynucleotide including a region that encodes an endoglucanase catalytic domain which includes: (a) a nucleotide sequence that encodes a polypeptide including an amino acid sequence represented by SEQ ID NO: 1;
(b) a nucleotide sequence that encodes a polypeptide including an amino acid sequence in which at least one amino acid is deleted, substituted, or added in the amino acid sequence represented by SEQ ID NO: 1, and having hydrolytic activity using p-nitrophenyl-β-D-cellobioside as a substrate at least under conditions of a temperature of 100° C. and a pH of 5.5;
(c) a nucleotide sequence that encodes a polypeptide including an amino acid sequence having at least 70% sequence identity with the amino acid sequence represented by SEQ ID NO: 1, and having hydrolytic activity using p-nitrophenyl-β-D-cellobioside as a substrate at least under conditions of a temperature of 100° C. and a pH of 5.5;
(d) a nucleotide sequence having at least 70% sequence identity with a nucleotide sequence represented by SEQ ID NO: 2, and encoding a polypeptide having hydrolytic activity using p-nitrophenyl-β-D-cellobioside as a substrate at least under conditions of a temperature of 100° C. and a pH of 5.5; or
(e) a nucleotide sequence of a polynucleotide which hybridizes with a polynucleotide including a nucleotide sequence represented by SEQ ID NO: 2 under a stringent condition, and being a nucleotide sequence that encodes a polypeptide having hydrolytic activity using p-nitrophenyl-β-D-cellobioside as a substrate at least under conditions of a temperature of 100° C. and a pH of 5.5.

[4] The polynucleotide according to the aforementioned aspect [3], which is a polynucleotide including the aforementioned nucleotide sequence of (a), wherein the aforementioned polynucleotide uses p-nitrophenyl-β-D-cellobioside as a substrate, and may also use at least one selected from the group consisting of β-glucan, lichenan, carboxymethyl cellulose, and phosphoric acid swollen Avicel as a substrate; or which is a polynucleotide including any one of the aforementioned nucleotide sequences of (b) to (e), wherein the aforementioned polypeptide may also use at least one selected from the group consisting of β-glucan, lichenan, carboxymethyl cellulose, and phosphoric acid swollen Avicel as a substrate.

[5] An expression vector, which is incorporated with the polynucleotide according to the aforementioned aspect [3] or [4], and which is able to express a polypeptide having glycoside hydrolysis activity in a host cell.

[6] A transformant, which is introduced with the expression vector according to the aforementioned aspect [5].

[7] The transformant according to the aforementioned aspect [6], which is a eukaryotic microbe.

[8] A method for producing a hyperthermostable endoglucanase, the method including a step of producing a hyperthermostable endoglucanase in the transformant according to the aforementioned aspect [6] or [7].

[9] A glycoside hydrolase mixture, including the hyperthermostable endoglucanase according to the aforementioned aspect [1] or [2], a hyperthermostable endoglucanase encoded by the polynucleotide according to the aforementioned aspect [3] or [4], or a hyperthermostable endoglucanase produced by the method for producing a hyperthermostable endoglucanase according to the aforementioned aspect [8], and at least one or more types of other glycoside hydrolases.

[10] A method for producing a lignocellulose degradation product, the method including a step of producing a lignocellulose degradation product by bringing a material composed of lignocellulose including cellulose into contact with the hyperthermostable endoglucanase according to the aforementioned aspect [1] or [2], a hyperthermostable endoglucanase encoded by the polynucleotide according to the aforementioned aspect [3] or [4], the transformant according to the aforementioned aspect [6] or [7], a hyperthermostable endoglucanase produced by the method for producing a hyperthermostable endoglucanase according to the aforementioned aspect [8], or the glycoside hydrolase mixture according to the aforementioned aspect [9].

Furthermore, the present invention relates to the following aspects.
(1) A hyperthermostable endoglucanase including an endoglucanase catalytic domain, the endoglucanase catalytic domain including: (A) a polypeptide including an amino acid sequence represented by SEQ ID NO: 1;
(B) a polypeptide including an amino acid sequence in which at least one amino acid is deleted, substituted, or added in the amino acid sequence represented by SEQ ID NO: 1, and having hydrolytic activity using p-nitrophenyl-β-D-cellobioside as a substrate at least under conditions of a temperature of 100° C. and a pH of 5.5; or
(C) a polypeptide including an amino acid sequence having at least 70% sequence identity with the amino acid sequence represented by SEQ ID NO: 1, and having hydrolytic activity using p-nitrophenyl-β-D-cellobioside as a substrate at least under conditions of a temperature of 100° C. and a pH of 5.5.
(2) The hyperthermostable endoglucanase according to the aspect (1), further having hydrolytic activity for β-glucan under conditions of a temperature of 100° C. and a pH of 4.5.
(3) A polynucleotide including a region that encodes an endoglucanase catalytic domain which includes: (a) a nucleotide sequence that encodes a polypeptide including an amino acid sequence represented by SEQ ID NO: 1;
(b) a nucleotide sequence that encodes a polypeptide including an amino acid sequence in which at least one amino acid is deleted, substituted, or added in the amino acid sequence represented by SEQ ID NO: 1, and having hydrolytic activity using p-nitrophenyl-β-D-cellobioside as a substrate at least under conditions of a temperature of 100° C. and a pH of 5.5;
(c) a nucleotide sequence that encodes a polypeptide including an amino acid sequence having at least 70% sequence identity with the amino acid sequence represented by SEQ ID NO: 1, and having hydrolytic activity using p-nitrophenyl-β-D-cellobioside as a substrate at least under conditions of a temperature of 100° C. and a pH of 5.5;
(d) a nucleotide sequence having at least 70% sequence identity with a nucleotide sequence represented by SEQ ID NO: 2, and encoding a polypeptide having hydrolytic activity using p-nitrophenyl-β-D-cellobioside as a substrate at least under conditions of a temperature of 100° C. and a pH of 5.5; or
(e) a nucleotide sequence of a polynucleotide which hybridizes with a polynucleotide including a nucleotide sequence represented by SEQ ID NO: 2 under a stringent condition, and being a nucleotide sequence that encodes a polypeptide having hydrolytic activity using p-nitrophenyl-β-D-cellobioside as a substrate at least under conditions of a temperature of 100° C. and a pH of 5.5.
(4) The polynucleotide according to the aspect (3), wherein the aforementioned polypeptide further has hydrolytic activity for β-glucan under conditions of a temperature of 100° C. and a pH of 4.5.
(5) An expression vector, which is incorporated with the polynucleotide according to the aspect (3) or (4), and which is able to express a polypeptide having glycoside hydrolysis activity in a host cell.
(6) A transformant, which is introduced with the expression vector according to the aspect (5).
(7) The transformant according to the aspect (6), which is a eukaryotic microbe.
(8) A method for producing a hyperthermostable endoglucanase, the method including a step of producing a hyperthermostable endoglucanase in the transformant according to the aspect (6) or (7).
(9) A glycoside hydrolase mixture, including the hyperthermostable endoglucanase according to the aspect (1) or (2), a hyperthermostable endoglucanase encoded by the polynucleotide according to the aspect (3) or (4), or a hyperthermostable endoglucanase produced by the method for producing a hyperthermostable endoglucanase according to the aspect (8), and at least one or more types of other glycoside hydrolases.
(10) A method for producing a lignocellulose degradation product, the method including a step of producing a lignocellulose degradation product by bringing a material composed of lignocellulose including cellulose into contact with the hyperthermostable endoglucanase according to the aspect (1) or (2), a hyperthermostable endoglucanase encoded by the polynucleotide according to the aspect (3) or (4), the transformant according to the aspect (6) or (7), a hyperthermostable endoglucanase produced by the method for producing a hyperthermostable endoglucanase according to the aspect (8), or the glycoside hydrolase mixture according to the aspect (9).

Effects of the Invention

The hyperthermostable endoglucanase according to the present invention has hydrolytic activity using p-nitrophenyl-β-d-cellobioside (hereinafter, may to be abbreviated as PNPC) as a substrate at least under conditions of a temperature of 100° C. and a pH of 5.5. For this reason, the aforementioned hyperthermostable endoglucanase is suitable for a hydrolysis process of celluloses in high temperature conditions.

In addition, the polynucleotide, the expression vector incorporated with the aforementioned polynucleotide and the transformant introduced with the aforementioned expression vector according to the present invention are suitably used for the production of the hyperthermostable endoglucanase according to the present invention.

BRIEF DESCRIPTION OF THE DRAWINGS

FIG. 1 is an alignment representation of the amino acid sequence (SEQ ID NO: 1) of the polypeptide (AR19M-113-4) encoded by the open reading frame AR19M-113 and the amino acid sequence (SEQ ID NO: 6) of a glycoside hydrolase 12 (GH12) of *Thermofilum pendens* strain Hrk 5 which is predicted to be an endoglucanase.

It is a diagram of the relative value of the hydrolysis activity for PNPC after a certain time of preincubation at 80 to 99° C. (relative value (in percentage) when the activity of an untreated group (with no preincubation) was regarded as 100%) which is shown for the respective preincubation time.

Figure 7:
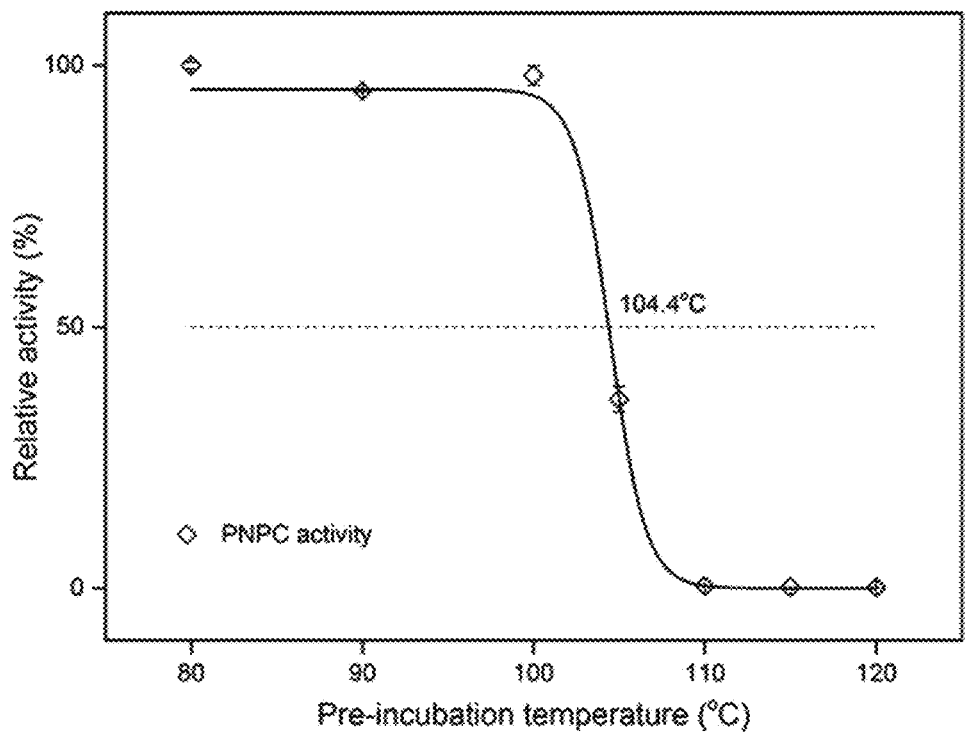

FIG. 7 is a diagram showing the measurement results of the thermal degradation temperature $T_m$ of the AR19M-113-4 protein expressed in *E. coli* in Example 1.

DESCRIPTION OF THE EMBODIMENT

[Hyperthermostable Endoglucanase]

Many microorganisms including filamentous fungi, bacteria and archaea are difficult to culture, and about 99% of the microorganisms living in the microbial environments such as soil are said to be unknown microbes. In particular, the culturing of microorganisms living in a high temperature environment is extremely difficult, and it is thought that merely 0.1% or less of the microorganisms living in soils have been isolated and cultured with the currently available microbial culturing techniques. This difficulty to culture such microorganisms living in high temperature soils is one factor to hinder the development of thermostable enzymes.

In recent years, because of the development of the next generation giga sequencer enabling large amount sequencing of giga base pairs, it has become possible to conduct the whole genome sequencing of the microbiota contained in soil and the like. Using this analysis technology, the metagenomic analysis method has been proposed in which the genomic DNA of a microbial group is prepared from an environmental sample such as soil, the genomes of the group having nonuniform and miscellaneous genomic organizations are directly and comprehensively sequenced, and the sequenced data are assembled by a parallel computer, so as to thereby reconstruct the genomic sequences of the microbiota. This has contributed to the rapid progress in the genome sequencing of hardly culturable microorganisms.

As shown in Example 1 described later, the inventors of the present invention extracted the genomic DNA (metagenomic DNA) of the microbial groups collected from high temperature hot spring soils (for example, hot spring water of 58 to 78° C. that contained soil, mud, microbial mats, biofilms and the like may be mentioned), and conducted shotgun sequencing and annotation of the metagenomic DNA. By so doing, open reading frames (ORFs) encoding the amino acid sequences similar to known endoglucanase enzymes (that is, the Expectation value (E-value) of less than 1e-$^{20}$) were obtained. Of these ORFs, primers were designed based on the nucleotide sequence information of 52 ORFs in which the presence of endoglucanase catalytic domain could be verified, and gene candidates were cloned from the metagenomic DNA of the high temperature hot spring soils by the PCR method. The PCR-cloned DNAs were incorporated into *E. coli*, and proteins encoded by the aforementioned nucleotide sequences were expressed. These were subjected to functional screenings by assays on the carboxymethyl cellulose (hereinafter, may be abbreviated as CMC) hydrolysis activity. In the end, hyperthermostable endoglucanases having glycoside hydrolysis activity (hereinafter, may be referred to as "AR19M-113-4") were obtained from these ORFs. The amino acid sequence of AR19M-113-4 and the nucleotide sequence encoding the amino acid sequence of AR19M-113-4 are represented by SEQ ID NO: 1 and SEQ ID NO: 2, respectively.

As shown in Example 1 <10> described later, AR19M-113-4 exhibited particularly high hydrolysis activity for lichenan and β-glucan, also exhibited high degradation activity for carboxymethyl cellulose (CMC) and PNPC, and also exhibited hydrolysis activity for phosphoric acid swollen Avicel (PSA) which is a non-crystalline cellulose, while exhibiting almost no degradation activity for xylan, xyloglucan, laminarin, PNPG (p-nitrophenyl-β-D-glucopyranoside), PNPX (p-nitrophenyl-β-D-xylopyranoside), and PNPL (p-nitrophenyl-β-D-lactopyranoside).

In other words, AR19M-113-4 is a hyperthermostable endoglucanase exhibiting high specificity for substrates in which β-1,3 bonds are partially mixed within β-1,4-linked glucans (for example, β-glucans, lichenan, and the like), and substrates composed of β-1,4-linked glucans (for example, crystalline celluloses such as PNPC, Avicel, bacterial microcrystalline cellulose (hereinafter, may be abbreviated as BMCC), and filter paper, CMC, phosphoric acid swollen Avicel (hereinafter, may be abbreviated as PSA), cellobiose, and the like).

The amino acid sequence of AR19M-113-4 was searched in publicly known amino acid sequence databases, resulting that the amino acid sequence showing the highest sequence identity was of a protein (Genbank: YP_921079.1) (SEQ ID NO: 6) which is predicted to be an endoglucanase belonging to the glycoside hydrolase 12 (GH12) family of a thermophilic archaeon in the phylum Crenarchaeota, *Thermofilum pendens* strain Hrk 5, with sequence identity (homology) of 35% in full length and 41% in the GH12 catalytic domain. From the substrate specificity and the sequence identity of the amino acid sequence with that of the already known proteins, it is clear that AR19M-113-4 is a novel endoglucanase belonging to the GH12 family.

AR19M-113-4 has hydrolytic activity using PNPC as a substrate at least under conditions of a temperature of 100° C. and a pH of 5.5. Actually, as shown in Example 1 <11> described later, AR19M-113-4 exhibits PNPC hydrolysis activity within a temperature range from 40 to 130° C., and exhibits strong PNPC hydrolysis activity within a temperature range from 85 to 120° C. More specifically, the PNPC hydrolysis activity of AR19M-113-4 at a pH of 5.5 using PNPC as a substrate tended to be increased as the temperature was increased within a range from 40 to 110° C. and tended to be decreased rapidly when the temperature exceeded 115° C. In addition, the β-glucan degradation activity of AR19M-113-4 at a pH of 4.5 using β-glucan as a substrate tends to increase as the temperature increases within a range from 60 to 105° C. and decreases rapidly when the temperature exceeded 100° C., and exhibits strong β-glucan degradation activity within a temperature range from 80 to 100° C.

Further, as another aspect of AR19M-113-4 expressed in *E. coli* as a host, it has high glycoside hydrolysis activity under conditions of a temperature of 110° C. and a pH of 4.5 to 6.5, and exhibits glycoside hydrolysis activity within a wide temperature range of 40 to 130° C. and within a wide pH range of 4 to 8.

In addition, as shown in Example 1 <13> described later, the thermal stability (half life of the enzymatic activity) of AR19M-113-4 is 24 hours or more from 80 to 90° C., about 35 hours at 95° C., and 12 to 13 hours at 99° C., showing that AR19M-113-4 is an endoglucanase exhibiting very high thermal stability within the ultra-high temperature range.

Generally, in a protein having some kind of bioactivity, one or two or more amino acids can be deleted, substituted, or added, without deteriorating the bioactivity. In other words, also in AR19M-113-4, one or two or more amino acids can be deleted, substituted, or added, without causing loss of glycoside hydrolysis activity.

That is, the hyperthermostable endoglucanase according to the present invention is a hyperthermostable glycoside hydrolase having an endoglucanase catalytic domain which includes any one of the following (A) to (C):
(A) a polypeptide including an amino acid sequence represented by SEQ ID NO: 1 (that is, AR19M-113-4);
(B) a polypeptide including an amino acid sequence in which at least one amino acid is deleted, substituted, or added in the amino acid sequence represented by SEQ ID NO: 1, as well as having hydrolysis activity using PNPC as a substrate at least under conditions of a temperature of 100° C. and a pH of 5.5; or
(C) a polypeptide including an amino acid sequence having at least 70% sequence identity with the amino acid sequence represented by SEQ ID NO: 1, as well as having hydrolysis activity using PNPC as a substrate at least under conditions of a temperature of 100° C. and a pH of 5.5.

In the present invention and the description of this application, a "polypeptide in which an amino acid is deleted" means that a portion of the amino acids which constitute the polypeptide is missing (that is, removed).

In the present invention and the description of this application, a "polypeptide in which an amino acid is substituted" means that an amino acid which constitutes the polypeptide is replaced with a different amino acid.

In the present invention and the description of this application, a "polypeptide in which an amino acid is added" means that a new amino acid is inserted within the polypeptide.

In the present invention and the description of this application, the expression "having activity" or "exhibiting activity" refers to an action on at least one substrate and means that a significant difference occurs in the hydrolyzed amount of reducing ends of the substrate or the color reaction as compared to the negative control. Therefore, the expression "having glycoside hydrolysis activity" refers to an action on at least one of substrates in which β-1,3 bonds are partially mixed within β-1,4-linked glucans (for example, β-glucans, lichenan, and the like) or substrates composed of β-1,4-linked glucans (for example, crystalline celluloses such as PNPC, Avicel, BMCC, and filter paper, CMC, PSA, cellobiose, and the like), and means that a significant difference occurs in the hydrolyzed amount of reducing ends of the substrate or the color reaction as compared to the negative control.

In addition, as another aspect, the expression "having glycoside hydrolysis activity" refers to an action on at least PNPC as a substrate under condition of a pH of 5.5 within a temperature range of 40 to 130° C. to have a hydrolysis activity of 1.0 U/mg or more.

As yet another aspect, the expression "having glycoside hydrolysis activity" refers to an action on at least β-glucan as a substrate under condition of a pH of 4.5 within a temperature range of 60 to 105° C. to have a hydrolysis activity of 1.0 U/mg or more.

In the aforementioned polypeptide of (B), the number of amino acids to be deleted, substituted, or added in the amino acid sequence represented by SEQ ID NO: 1 is preferably from 1 to 20, more preferably from 1 to 10, and still more preferably from 1 to 5.

In the aforementioned polypeptide of (C), the sequence identity with the amino acid sequence represented by SEQ ID NO: 1 is not particularly limited as long as it is 70% or greater but less than 100%, although it is preferable to be 75% or greater but less than 100%, more preferably 80% or greater but less than 100%, still more preferably 85% or greater but less than 100%, still more preferably 90% or greater but less than 100%, and particularly preferably 95% or greater but less than 100%.

It should be noted that the sequence identity (homology) between a pair of amino acid sequences is obtained such that: two amino acid sequences are juxtaposed while having gaps in some parts accounting for insertion and deletion so that the largest numbers of corresponding amino acids can be matched, and the sequence identity is deemed to be the proportion of the matched amino acids relative to the whole amino acid sequences excluding the gaps, in the resulting alignment. The sequence identity between a pair of amino acid sequences can be obtained by using a variety of homology search software publicly known in the art. The sequence identity value between amino acid sequences in the present invention is obtained by calculation on the basis of an alignment obtained from a publicly known homology search software BLASTP.

The aforementioned polypeptides of (B) and (C) may be those that are artificially designed, or may also be homologues of AR19M-113-4 and the like, or partial proteins thereof.

The aforementioned polypeptides of (A) to (C) may be respectively synthesized in a chemical manner based on the amino acid sequence, or may also be produced by a protein expression system using the polynucleotide according to the present invention that will be described later. In addition, the aforementioned polypeptides of (B) and (C) can also be respectively synthesized artificially based on a polypeptide including the amino acid sequence represented by SEQ ID NO: 1, by using a genetic recombination technique to introduce amino acid mutation(s).

The aforementioned polypeptides of (A) to (C) have hydrolysis activities using PNPC as a substrate at least under conditions of a temperature of 100° C. and a pH of 5.5. For this reason, a hyperthermostable endoglucanase can be obtained by having any one of the aforementioned polypeptides of (A) to (C) as the endoglucanase catalytic domain.

The hyperthermostable endoglucanase according to the present invention uses substrates in which β-1,3 bonds are partially mixed within β-1,4-linked glucans and substrates composed of β-1,4-linked glucans.

Such substrates in which β-1,3 bonds are partially mixed within β-1,4-linked glucans can be exemplified by β-glucans, lichenan, and the like. Such substrates composed of β-1,4-linked glucans can be exemplified by crystalline celluloses such as PNPC, Avicel, bacterial microcrystalline cellulose (BMCC), and filter paper, CMC, PSA, cellobiose, and the like. The hyperthermostable endoglucanase according to the present invention is preferably capable of using, in addition to PNPC, at least one member selected from the group consisting of a β-glucan, lichenan, CMC, and PSA as a substrate; and is more preferably capable of using, in addition to PNPC, at least one member selected from the group consisting of a β-glucan, lichenan, and CMC as a substrate.

The hyperthermostable endoglucanase according to the present invention uses PNPC as a substrate, and may also use another type of glucan as a substrate. Examples of those that can also be used as a substrate by the hyperthermostable endoglucanase according to the present invention include PNPX, PNPG, p-nitrophenyl-α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside, p-nitrophenyl-β-D-galactopyranoside; a glucan composed of β-1,3 bonds and β-1,6 bonds such as laminarin; a glucan composed of β-1,3 bonds; and a glucan composed of β-1,6 bonds and an oligosaccharide composed of β-1,6 bonds such as gentiobiose.

The hyperthermostable endoglucanase according to the present invention preferably exhibits PNPC hydrolysis activity at least under conditions of a pH of 5.5 within a temperature range from 90 to 110° C., more preferably within a temperature range from 80 to 120° C., still more preferably within a temperature range from 70 to 130° C., and still more preferably within a temperature range from 40 to 130° C. The optimum temperature of the hyperthermostable endoglucanase according to the present invention in the case of using PNPC as a substrate is preferably within the range from 90 to 120° C. under a condition of a pH of 5.5, more preferably within the range from 100 to 120° C., and still more preferably within the range from 105 to 115° C.

The hyperthermostable endoglucanase according to the present invention preferably exhibits a degradation activity using β-glucan as a substrate at least under a condition of a pH of 4.5 within a temperature range from 90 to 100° C., more preferably within a temperature range from 80 to 105° C., still more preferably within a temperature range from 70 to 130° C., and still more preferably within a temperature range from 60 to 110° C. The optimum temperature of the hyperthermostable endoglucanase according to the present invention in the case of using a β-glucan as a substrate is preferably within the range from 85 to 105° C. under a condition of a pH of 4.5, and more preferably within the range from 90 to 105° C.

Although the optimum pH of the hyperthermostable endoglucanase according to the present invention varies depending on the reaction temperature and the substrate, it is within a pH range from 4.0 to 7.0. For example, the optimum pH at 90° C. in the case of using PNPC as a substrate is within a pH range from 5.5 to 7.0, and the optimum pH at 90° C. in the case of using β-glucan as a substrate is within a pH range from 4.0 to 5.0. As the hyperthermostable endoglucanase according to the present invention, those exhibiting glycoside hydrolysis activity at least within a pH range of 4.5 to 6.5 are preferred, and those exhibiting glycoside hydrolysis activity within a pH range of 4.0 to 8.0 are more preferred.

The hyperthermostable endoglucanase according to the present invention may also have xylanase activity, β-xylosidase activity, β-glucosidase activity, cellobiohydrolase activity, or the like, in addition to the aforementioned glycoside hydrolysis activity.

The hyperthermostable endoglucanase according to the present invention may be an enzyme solely consisting of an endoglucanase catalytic domain which includes any one of the aforementioned polypeptides of (A) to (C), or may further include other domains. Examples of other domains include a domain present in the known glycoside hydrolases other than the enzyme catalytic domain. For example, the hyperthermostable endoglucanase according to the present invention also includes enzymes obtained by substituting an enzyme catalytic domain in a publicly known glycoside hydrolase with the aforementioned polypeptides of (A) to (C).

If the hyperthermostable endoglucanase according to the present invention includes a domain other than the endoglucanase catalytic domain, it is also preferable to include a cellulose-binding module. The cellulose-binding module may be either on the upstream (N-end side) or the downstream (C-end side) of the endoglucanase catalytic domain.

In addition, the cellulose-binding module and the endoglucanase catalytic domain may be directly linked, or linked via a linker domain of an appropriate length. The hyperthermostable endoglucanase according to the present invention is preferably such that the cellulose-binding module is present on the upstream or the downstream of the endoglucanase catalytic domain via a linker domain, more preferably such that the cellulose-binding module is present on the upstream of the endoglucanase catalytic domain via a linker domain.

The cellulose-binding module contained in the hyperthermostable endoglucanase according to the present invention may suffice if it is a domain having an ability to bind to cellulose, for example, a domain having an ability to bind to PSA or a crystalline Avicel. The amino acid sequence thereof is not particularly limited. As the cellulose-binding module, for example, a cellulose-binding module of an already known protein or appropriately modified product thereof may be used. In addition, if the hyperthermostable endoglucanase according to the present invention has an endoglucanase catalytic domain and a cellulose-binding module, it is preferable that these are linked via a linker sequence. The amino acid sequence, the length, and the like, of the linker sequence are not particularly limited.

In addition, the hyperthermostable endoglucanase according to the present invention may also have a signal peptide enabling to transport it to a specific region to effect localization within a cell, or a signal peptide to effect extracellular secretion, at the N end or the C end. Such a signal peptide can be exemplified by an apoplastic transport signal peptide, an endoplasmic reticulum retention signal peptide, a nuclear transport signal peptide, a secretory signal peptide, or the like. The endoplasmic reticulum retention signal peptide can be exemplified by, for example, a signal peptide including a HDEL amino acid sequence, or the like. In those cases where the hyperthermostable endoglucanase according to the present invention has a signal peptide at the N end or the C end, the hyperthermostable endoglucanase expressed in a transformant can be secreted outside the cell, or can be localized in the intracellular endoplasmic reticulum, or the like.

In addition, the hyperthermostable endoglucanase according to the present invention may also be added with, for example, various types of tags at the N end or the C end, so as to enable easy and convenient purification in a case of the production using an expression system. Regarding such a tag, for example, it is possible to use a tag for usual use in the expression or purification of a recombinant protein, such as a His tag, a HA (hemagglutinin) tag, a Myc tag, and a Flag tag.

[Polynucleotide that Encodes Hyperthermostable Endoglucanase]

The polynucleotide according to the present invention encodes the hyperthermostable endoglucanase according to the present invention. The aforementioned hyperthermostable endoglucanase can be produced by using the expression system of a host made by introducing an expression vector incorporated with the polynucleotide into the host.

More specifically, the polynucleotide according to the present invention is a polynucleotide having a region that encodes an endoglucanase catalytic domain which includes any one of the following nucleotide sequences (a) to (e).

(a) A nucleotide sequence that encodes a polypeptide including the amino acid sequence represented by SEQ ID NO: 1;
(b) a nucleotide sequence that encodes a polypeptide including an amino acid sequence in which at least one amino acid is deleted, substituted, or added in the amino acid sequence represented by SEQ ID NO: 1, as well as having hydrolysis activity using PNPC as a substrate at least under conditions of a temperature of 100° C. and a pH of 5.5;

(c) a nucleotide sequence that encodes a polypeptide including an amino acid sequence having at least 70% sequence identity with the amino acid sequence represented by SEQ ID NO: 1, as well as having hydrolysis activity using PNPC as a substrate at least under conditions of a temperature of 100° C. and a pH of 5.5;

(d) a nucleotide sequence having at least 70% sequence identity with a nucleotide sequence represented by SEQ ID NO: 2, as well as encoding a polypeptide having hydrolysis activity using PNPC as a substrate at least under conditions of a temperature of 100° C. and a pH of 5.5; or (e) a nucleotide sequence of a polynucleotide which hybridizes with a polynucleotide including a nucleotide sequence represented by SEQ ID NO: 2 under a stringent condition, as well as being a nucleotide sequence that encodes a polypeptide having hydrolysis activity using PNPC as a substrate at least under conditions of a temperature of 100° C. and a pH of 5.5.

It should be noted that in the present invention and the description of this application, a "polynucleotide in which a nucleotide is deleted" means that a portion of the nucleotides which constitute the polynucleotide is missing (that is, removed).

In the present invention and the description of this application, a "polynucleotide in which a nucleotide is substituted" means that a nucleotide which constitutes the polynucleotide is replaced with a different nucleotide.

In the present invention and the description of this application, a "polynucleotide in which a nucleotide is added" means that a new nucleotide is inserted within the polynucleotide.

In the present invention and the description of this application, the term "under a stringent condition" can be exemplified by the method described in Molecular Cloning—A Laboratory Manual Third Edition (Sambrook et al., Cold Spring Harbor Laboratory Press). The example thereof includes a condition in which hybridization is performed by incubation in a hybridization buffer including 6×SSC (composition of 20×SSC: 3M sodium chloride, 0.3M citric acid solution, and pH7.0), 5×Denhardt's solution (composition of 100×Denhardt's solution: 2 mass % bovine serum albumin, 2 mass % Ficoll, 2 mass % polyvinylpyrrolidone), 0.5 mass % SDS, 0.1 mg/mL salmon sperm DNA, and 50% formamide, at a temperature of 42 to 70° C. for several hours to overnight. The washing buffer for use in the washing after the incubation is preferably 1×SSC solution containing 0.1 mass % SDS, and more preferably 0.1×SSC solution containing 0.1 mass % SDS.

In the aforementioned nucleotide sequences of (a) to (e), it is preferable to select a degenerate codon having high frequency of usage in the host. For example, the aforementioned nucleotide sequence of (a) may be either the nucleotide sequence represented by SEQ ID NO: 2, or a nucleotide sequence altered to have a codon having high frequency of usage in the host without changing the amino acid sequence to be encoded by the nucleotide sequence represented by SEQ ID NO: 2. These codons can be altered by a publicly known gene sequence modification technique or artificial gene synthesis.

The polynucleotide including the nucleotide sequence represented by SEQ ID NO: 2 may be synthesized in a chemical manner based on the nucleotide sequence information, or may be obtained as a full length of a gene that encodes AR19M-113-4 (may be referred to as "AR19M-113-4 gene" or "gene clone AR19M-113-4") or a partial region thereof including the endoglucanase catalytic domain (that is, a region encoding a partial region composed of 169 amino acid residues from proline (P) at position 113 to threonine (T) at position 281 in SEQ ID NO: 1) from the natural world by using a genetic recombination technique. The full length of the AR19M-113-4 gene or the partial region thereof can be obtained by, for example, collecting a sample containing microorganisms from the natural world, and conducting PCR using the genomic DNA recovered from the sample as a template, with a forward primer and a reverse primer designed on the basis of the nucleotide sequence represented by SEQ ID NO: 2 by a conventional method. The cDNA synthesized by a reverse transcription reaction using mRNA recovered from the sample as a template may also be used as a template. Note that, it is preferable that the sample for recovering the nucleic acid serving as a template is a sample collected from a high temperature environment such as hot spring soil.

In the aforementioned nucleotide sequence of (d), the sequence identity with the nucleotide sequence represented by SEQ ID NO: 2 is not particularly limited as long as it is 70% or greater but less than 100%, although it is preferable to be 75% or greater but less than 100%, more preferably 80% or greater but less than 100%, still more preferably 85% or greater but less than 100%, still more preferably 90% or greater but less than 100%, and particularly preferably 95% or greater but less than 100%.

Note that, the sequence identity (homology) between a pair of nucleotide sequences is obtained such that: two nucleotide sequences are juxtaposed while having gaps in some parts accounting for insertion and deletion so that the largest numbers of corresponding nucleotides can be matched, and the sequence identity is deemed to be the proportion of the matched nucleotides relative to the whole nucleotide sequences excluding gaps, in the resulting alignment. The sequence identity between a pair of nucleotide sequences can be obtained by using a variety of homology search software publicly known in the art. The sequence identity value between nucleotide sequences in the present invention is obtained by calculation on the basis of an alignment obtained from a publicly known homology search software BLASTN.

For example, the polynucleotide including the aforementioned nucleotide sequence of (b), (c), or (d) can be respectively synthesized artificially by deleting, substituting, or adding one or two or more nucleotides in a polynucleotide including the nucleotide sequence represented by SEQ ID NO: 2. In addition, the aforementioned nucleotide sequence of (b), (c), or (d) may also be a full length sequence of a homologous gene of the AR19M-113-4 gene or a partial sequence thereof. The homologous gene of the AR19M-113-4 gene can be obtained by a genetic recombination technique for use in obtaining a homologous gene of a gene whose nucleotide sequence has been already known.

The polynucleotide according to the present invention may have only the region that encodes the endoglucanase catalytic domain, or may also have a region that encodes a cellulose-binding module, a linker sequence, various types of signal peptides, various types of tags, or the like, in addition to the aforementioned region.

[Expression Vector]

The expression vector according to the present invention is incorporated with the aforementioned polynucleotide according to the present invention, and is able to express a polypeptide having hydrolysis activity using PNPC as a substrate at least under conditions of a temperature of 100° C. and a pH of 5.5 in a host cell. That is, it is an expression vector which is incorporated with the aforementioned polynucleotide according to the present invention in a state where the aforementioned hyperthermostable endoglucanase according to the present invention can be expressed. More specifically, it is necessary for the expression vector to be incorporated with an expression cassette including, from the upstream, DNA having a promoter sequence, the aforementioned polynucleotide according to the present invention, and DNA having a terminator sequence. It should be noted that the incorporation of the polynucleotide into the expression vector can be performed by using a well-known genetic recombination technique. It is also possible to use a commercially available expression vector preparation kit for the incorporation of the polynucleotide into the expression vector.

In the present invention and the description of this application, an "expression vector" is a vector including, from the upstream, DNA having a promoter sequence, DNA having a sequence for incorporating foreign DNA, and DNA having a terminator sequence.

The expression vector may be a vector to be introduced into a prokaryotic cell such as *E. coli*, or to be introduced into a eukaryotic cell such as a yeast, a filamentous fungus, a cultured insect cell, a cultured mammalian cell, or a plant cell. Regarding such an expression vector, an arbitrary expression vector for usual use can be adopted corresponding to the respective host.

It is preferable that the expression vector according to the present invention is an expression vector incorporated with not only the aforementioned polynucleotide according to the present invention but also a drug resistance gene or the like. This is because it makes it easy to screen host cells transformed by the expression vector and untransformed host cells.

The drug resistance gene can be exemplified by a kanamycin resistance gene, a hygromycin resistance gene, a bialaphos resistance gene, or the like.

[Transformant]

The transformant according to the present invention is introduced with the above-mentioned expression vector according to the present invention. In the aforementioned transformant, the hyperthermostable endoglucanase according to the present invention can be expressed. The host to introduce the expression vector may be a prokaryotic cell such as *E. coli* or a eukaryotic cell such as a yeast, a filamentous fungus, a cultured insect cell, a cultured mammalian cell, or a plant cell. That is, the transformant according to the present invention is *E. coli*, a yeast, a filamentous fungus, a cultured insect cell, a cultured mammalian cell, a plant cell, or the like which is introduced with the expression vector according to the present invention.

By culturing a transformant of *E. coli*, the hyperthermostable endoglucanase according to the present invention can be produced more easily and conveniently with high yield. On the other hand, because proteins are glycosylated in eukaryotic cells, a hyperthermostable endoglucanase which is more thermostable can be produced by using a transformant of a eukaryotic cell rather than by using a transformant of a prokaryotic cell.

The method to produce the transformant using the expression vector is not particularly limited, and a method for usual use in the production of transformants can be conducted. The concerned method can be exemplified by a heat shock method, an *Agrobacterium*-mediated method, a particle gun method, an electroporation method, a PEG (polyethylene glycol) method, and the like. Of these, if the host is a plant cell, a particle gun method or an *Agrobacterium*-mediated method is preferred.

If a prokaryotic cell, a yeast, a filamentous fungus, a cultured insect cell, a cultured mammalian cell, or the like is used as a host, the obtained transformant is generally able to be cultured by a usual method in the same manner as that of the untransformed host.

[Method for Producing a Hyperthermostable Endoglucanase]

The method for producing a hyperthermostable endoglucanase according to the present invention is a method to produce a hyperthermostable endoglucanase in the aforementioned transformant according to the present invention. When culturing a transformant produced by using the expression vector incorporated with the aforementioned polynucleotide according to the present invention on the downstream of a promoter which has no ability to regulate the timing of the expression or the like, in the transformant, the hyperthermostable endoglucanase according to the present invention is expressed constitutively. On the other hand, for the transformant produced by using a so-called expression inducible promoter to induce the expression by means of a specific compound, temperature condition, or the like, the hyperthermostable endoglucanase is expressed in the concerned transformant by culturing the transformant and conducting an induction treatment suitable for the respective expression-inducing condition.

The hyperthermostable endoglucanase produced by the transformant may be used in a state of being retained in the transformant, or may be extracted/purified from the transformant.

The method to extract or purify the hyperthermostable endoglucanase from the transformant is not particularly limited as long as the method does not deteriorate the activity of the hyperthermostable endoglucanase, and the extraction can be done by a method for usual use in the extraction of a polypeptide from cells or biological tissues. The method can be exemplified by a method in which the transformant is immersed in an appropriate extraction buffer to extract the hyperthermostable endoglucanase, and thereafter the liquid extract and the solid residue are separated. The extraction buffer preferably contains a solubilizing agent such as a surfactant. If the transformant is a plant, the transformant may be previously shredded or crushed before immersing in an extraction buffer. Moreover, as the method for separating the liquid extract and the solid residue, for example, a publicly known solid-liquid separation treatment such as a filtration method, a compression filtration method, or a centrifugation treatment method may be used, or the transformant immersed in an extraction buffer may be squeezed. The hyperthermostable endoglucanase in the liquid extract can be purified by using a publicly known purification method such as a salting-out method, an ultrafiltration method, or a chromatography method.

If the hyperthermostable endoglucanase according to the present invention is expressed while the secretory signal peptide is held in the transformant, a solution containing the hyperthermostable endoglucanase can be easily and conveniently obtained by culturing the transformant and thereafter recovering a culture liquid supernatant made by removal of the transformant from the obtained culture product. Moreover, if the hyperthermostable endoglucanase according to the present invention has a tag such as a His tag, the hyperthermostable endoglucanase in a liquid extract or in a culture supernatant can be easily and conveniently purified by an affinity chromatography method using the tag.

In other words, the method for producing a hyperthermostable endoglucanase according to the present invention includes the culturing of the transformant according to the present invention to produce a hyperthermostable endoglucanase within the transformant, and, according to need, the extraction and purification of the hyperthermostable endoglucanase from the transformant.

[Glycoside Hydrolase Mixture]

The glycoside hydrolase mixture according to the present invention can also be used as a mixture containing the aforementioned hyperthermostable endoglucanase according to the present invention, or a hyperthermostable endoglucanase produced by the aforementioned method for producing a hyperthermostable endoglucanase according to the present invention, and at least one or more types of other glycoside hydrolases. The hyperthermostable endoglucanase produced by the aforementioned method for producing a hyperthermostable endoglucanase according to the present invention may be in a state of being included in the transformant, or may be extracted or purified from the transformant. By using the hyperthermostable endoglucanase according to the present invention as a mixture with other glycoside hydrolases in the reaction to hydrolyze polysaccharides, persistent lignocelluloses can be more efficiently degraded.

The other glycoside hydrolase than the aforementioned hyperthermostable endoglucanase to be contained in the glycoside hydrolase mixture is not particularly limited as long as it has lignocellulose hydrolysis activity. The other glycoside hydrolase than the aforementioned hyperthermostable endoglucanase to be contained in the glycoside hydrolase mixture can be exemplified by hemicellulases such as xylanase and β-xylosidase, cellobiohydrolase, β-glucosidase, endoglucanase, or the like. In addition to the hyperthermostable endoglucanase, the glycoside hydrolase mixture according to the present invention is preferably a mixture containing at least either one of glycoside hydrolases (i.e., a hemicellulase or an endoglucanase), and is more preferably a mixture containing both glycoside hydrolases (i.e., a hemicellulase and an endoglucanase). Among them, a mixture containing, in addition to the aforementioned hyperthermostable endoglucanase, at least one type of glycoside hydrolases selected from the group consisting of xylanase, β-xylosidase, cellobiohydrolase, and β-glucosidase is preferred; and a mixture containing, in addition to the aforementioned hyperthermostable endoglucanase, all of glycoside hydrolases (i.e., xylanase, β-xylosidase, cellobiohydrolase, and β-glucosidase) is more preferred.

The other glycoside hydrolase to be contained in the glycoside hydrolase mixture is preferably a thermostable glycoside hydrolase having glycoside hydrolase activity at least at a temperature of 85° C., and more preferably a thermostable glycoside hydrolase having glycoside hydrolase activity at a temperature of 70 to 90° C. When all the enzymes contained in the glycoside hydrolase mixture are thermostable (for example, the optimum temperature of the enzyme activity or the thermal denaturation temperature of the enzyme protein is 70° C. or higher), the reaction to degrade lignocelluloses with the glycoside hydrolase mixture can be efficiently conducted under a high temperature condition. That is, if the glycoside hydrolase mixture contains only thermostable glycoside hydrolases, it becomes possible, by using the glycoside hydrolase mixture for a lignocellulose hydrolysis process, to conduct the lignocellulose hydrolysis reaction under a high temperature environment where the hydrolysis temperature is from 70 to 90° C. (high temperature hydrolysis). With this high temperature hydrolysis, the amount of enzymes and the time for hydrolysis can be remarkably reduced, and the cost for hydrolysis can be largely cut out.

[Method for Producing a Lignocellulose Degradation Product]

The method for producing a lignocellulose degradation product according to the present invention is a method to obtain a lignocellulose degradation product by hydrolyzing a material composed of lignocellulose containing cellulose with the hyperthermostable endoglucanase according to the present invention to produce oligosaccharides. More specifically, a lignocellulose degradation product is produced by bringing a material composed of lignocellulose containing hemicellulose or cellulose into contact with the hyperthermostable endoglucanase according to the present invention, the transformant according to the present invention, a hyperthermostable endoglucanase produced by the method for producing a hyperthermostable endoglucanase according to the present invention, or the glycoside hydrolase mixture according to the present invention.

More specifically, the term "lignocellulose degradation product" used herein refers to a product obtained by cleavage of the glycoside bond of a hemicelluloses or cellulose.

Another aspect of the method for producing a lignocellulose degradation product according to the present invention is a method in which a material composed of lignocellulose containing hemicellulose or cellulose is brought into contact with the hyperthermostable endoglucanase according to the present invention, the transformant according to the present invention, or a hyperthermostable endoglucanase produced by the method for producing a hyperthermostable endoglucanase according to the present invention, to thereby produce a product obtained by cleavage of the glycoside bond of cellulose mainly.

Yet another aspect of the method for producing a lignocellulose degradation product according to the present invention is a method in which a material composed of lignocellulose containing hemicellulose or cellulose is brought into contact with the glycoside hydrolase mixture according to the present invention, to thereby produce which is a hemicellulose or cellulose degradation product.

The material composed of lignocellulose containing hemicellulose or cellulose is not particularly limited as long as it contains hemicellulose or cellulose. Such a material can be exemplified by cellulose-based biomass such as a weed and an agricultural waste, used paper, or the like. The aforementioned material composed of lignocellulose containing hemicellulose or cellulose is preferably subjected to a physical treatment such as crushing or shredding, a chemical treatment with an acid, alkali, or the like, or a treatment such as immersing in an appropriate buffer or a dissolution treatment, or the like, prior to being brought into contact with the hyperthermostable endoglucanase according to the present invention.

The reaction condition of the hydrolysis reaction of hemicellulose or cellulose by means of the hyperthermostable endoglucanase according to the present invention may suffice if the condition allows the hyperthermostable endoglucanase to exhibit glycoside hydrolysis activity. For example, it is preferable to conduct the reaction at a temperature of 40 to 130° C. and a pH of 4.0 to 8.0, more preferable to conduct the reaction at a temperature of 80 to 130° C. and a pH of 4.0 to 8.0, still more preferable to conduct the reaction at a temperature of 80 to 100° C. and a pH of 4.0 to 7.0, and still more preferable to conduct the reaction at a temperature of 90 to 105° C. and a pH of 4.5 to 6.5. The reaction time of the hydrolysis reaction is appropriately adjusted in consideration of the type, the method of pretreatment, the amount, or the like, of the material composed of lignocellulose containing hemicellulose or cellulose, to be supplied to the hydrolysis. For example, the hydrolysis reaction can be carried out in a reaction time of 10 minutes to 100 hours, and 1 to 100 hours when degrading the cellulose-based biomass.

For the hydrolysis reaction of the aforementioned material composed of lignocellulose, it is also preferable to use at least one or more types of other glycoside hydrolases simultaneously or separately, in addition to the hyperthermostable endoglucanase according to the present invention. The other glycoside hydrolase may be the same as the glycoside hydrolase that can be contained in the aforementioned glycoside hydrolase mixture, and it is preferable to be a thermostable glycoside hydrolase having glycoside hydrolase activity at least at a temperature of 85° C., and preferably at least at a temperature of 70 to 90° C. In addition, one aspect of the method for producing a lignocellulose degradation product is the use of the hyperthermostable endoglucanase according to the present invention, the transformant according to the present invention, or a hyperthermostable endoglucanase produced by the method for producing a hyperthermostable endoglucanase according to the present invention, and another aspect is the use of the aforementioned glycoside hydrolase mixture.

EXAMPLES

Next is a more detailed description of the present invention with reference to Examples. However, the present invention is not to be limited to the following Examples.

Example 1

Cloning of Novel Hyperthermostable Endoglucanase from Hot Spring Soil

<1> DNA Extraction from Hot Spring Soil and Whole Genome Sequencing (WGS)

With the purpose of searching for genes of novel hyperthermostable endoglucanase exhibiting activity at a temperature of 70 to 99° C., soil DNA was collected from neutral to weakly alkaline hot springs and subjected to nucleotide sequencing of the metagenomic DNA of the microbiota constituting the soil.

As the soil sample from neutral to weakly alkaline hot springs, hot spring water containing soil, clay, and biomat was collected from five sampling points having gushing high temperature outdoor hot springs in three areas in Japan (metagenomic DNA samples N2, AR19, AR15, OJ1, and H1). These hot spring soil samples were within a range of temperature from 58 to 78° C. and a pH of 7.2 to 8 at the time of the collection.

DNA was extracted from 10 g of each of the collected hot spring soil samples by using the DNA extraction kit (ISOIL Large for Beads ver. 2, manufactured by NIPPON GENE Co., Ltd.). The extracted DNA was subjected to shotgun sequencing of the metagenomic DNA by using the GS FLX Titanium 454 sequencer manufactured by Roche Diagnostics K.K. and the HiSeq 2000 sequencer manufactured by Illumina, Inc. 5 μg of the extracted DNA and the product amplified by using the genomic DNA amplification kit (GenomiPhi V2 DNA Amplification Kit, manufactured by GE Healthcare) were subjected to the metagenomic DNA sequencing using the 454 sequencer and the HiSeq 2000 sequencer, respectively.

In the sequencing by the HiSeq 2000 sequencer, DNA libraries and reagents were poured into the flow cell by using the cBot manufactured by Illumina, Inc., to automatically form a cluster having the identical sequence within the flow cell from a single DNA molecule. Paired-end sequencing of 101 bp was conducted using the HiSeq 2000 sequencer to obtain metagenomic sequence data.

The metagenomic DNA sequencing was carried out using the hot spring soil sample AR19. By so doing, a data set of the whole genome sequence (WGS) was obtained in which an average read length of 396 bp, a total number of reads of 2,766,332, and a total quantity of sequenced genomes of 1,106,243,280 bp were obtained with the 454 sequencer, and an average read length of 92.65 bp in paired-end reads, a total number of reads of 894,238,096, and a total quantity of sequenced genomes of 83,112,168,755 bp were obtained with the HiSeq 2000 sequencer, resulting in a total of 84.2 Gbp.

<2> Assembling and Statistics of Hot Spring Metagenomic Data

The nucleotide sequence that had been read by the 454 sequencer and the HiSeq 2000 sequencer was subjected to quality filtering and de novo assembly by using the CLC Genomics Workbench (ver. 5.5.1) manufactured by CLC bio. After the quality filtering, the total read length obtained with the 454 sequencer reached 1,084,400,576 bp, and the total read length of the nucleotide sequence data obtained with the HiSeq 2000 sequencer reached 81,323,692,563 bp. After the assembly, the number of contigs with a length of 500 bp or more was 967,925, and the overall length reached 419,787,603 bp. Of these, the maximum contig length was 287,641 bp.

<3> Prediction of Open Reading Frames (ORFs) of Endoglucanase

The sequences of EC numbers of 3.2.1.4 (cellulase), 3.2.1.21 (β-glucosidase), 3.2.1.37 (β-xylosidase), 3.2.1.91 (cellulose 1,4-β-cellobiosidase), and 3.2.1.8 (endo 1,4-β-xylanase) were downloaded from the UniProt database (the date of access: 2011 Dec. 9), and the proteome local database of these glycoside hydrolase genes was constructed. Using the annotation software Metagene (Noguchi et al., DNA Research, 2008, 15(6)), gene regions (=open reading frames) were predicted from the contig sequences obtained from the above-mentioned process <2> (Metagene option: −m). In order to extract the glycoside hydrolase gene from the predicted ORF, the aforementioned local database using BLASTP (blastall ver. 2.2.18) was referred to. Optional conditions of BLASTP were set such that: "Filter query sequence=false", "Expectation value (E)<1e$^{-20}$" [hereunder, the default values: Cost to open a gap=−1, Cost to extended gap=−1, X dropoff value for gapped alignment=0, Threshold for extending hits=0, and Word size=default], and the hit ORF sequences were collected as glycoside hydrolase genes. The collected nucleotide sequences included the genes of glycoside hydrolases such as cellulases, endohemicellulases, and debranching enzymes.

<4> Classification of Genes into Glycoside Hydrolase (GH) Families

The nucleotide sequences that had been collected in the above-mentioned process <3> were subjected to functional classification, with reference to the protein functional region sequence database of pfam HMMs (Pfam version 23.0 and HMMER v2.3; Finn et al., Nucleic Acids Research Database, 2010, Issue 38, p. D211-222). More specifically, the glycoside hydrolase (GH) families were determined for each of the nucleotide sequences that had been collected in the above-mentioned process <3> by the homology with the Pfam domain database by using the protein motif search program HMMER (Durbin et al., "The theory behind profile HMMs. Biological sequence analysis: probabilistic models of proteins and nucleic acids", 1998, Cambridge University Press.; hmmpfam (Ver. 2.3.2), E-value cutoff <1e-5; Database=Pfam_fs (models that can be used to find fragments of the represented domains in a sequence.)). It should be noted that those that covered 70% or more of the sequence of GH catalytic domains were counted as enzyme genes belonging to the respective families.

From the sequence data of metagenome AR19 with a length of 84.2 Gbp, 602,589 ORFs were predicted by Metagene, and the number of full-length ORFs was 251,146.

312 ORFs hit as endoglucanase sequences by the homology search with BLASTP. Out of these 312 ORFs, 52 ORFs were predicted to be endoglucanase genes by the domain search with HMMER, whereas 260 ORFs either exhibited a coverage of the GH catalytic domain sequence of less than 70%, or did not hit any sequence in the pfam database. Both the initiation codon and the termination codon of a full-length ORF can be identified by Metagene.

The result of the GH family classification of 52 ORFs predicted as endoglucanase genes is shown in Table 1. As shown in Table 1, 21 full-length ORFs of endoglucanase genes belonging to the GH5 family, 2 full-length ORFs of endoglucanase genes belonging to the GH8 family, 6 full-length ORFs endoglucanase genes belonging to the GH9 family, and 4 full-length ORFs of endoglucanase genes belonging to the GH12 family were obtained from the metagenome AR19. Primers were designed for all of these full-length ORFs having been predicted as endoglucanase genes, and these genes were cloned from the hot spring soil metagenomic DNA by PCR. As a result, an endoglucanase gene was isolated from AR19M-113 which was an ORF belonging to the GH12 family and having an endoglucanase gene sequence.

TABLE 1

| AR19 metagenome | GH family classification of endoglucanase genes | | | | |
|---|---|---|---|---|---|
| | GH5 | GH8 | GH9 | GH12 | Total |
| Full-length ORFs | 21 | 2 | 6 | 4 | 33 |
| Incomplete ORFs | 13 | 2 | 3 | 1 | 19 |
| Total number of ORFs | 34 | 4 | 9 | 5 | 52 |

<5> Open Reading Frame AR19M-113

The open reading frame AR19M-113 encoded a polypeptide (SEQ ID NO: 1) including 309 amino acid residues and was a full-length sequence (SEQ ID NO: 2), such that the polypeptide started from methionine which was an amino acid residue at position 1, and the 3' end of the nucleotide sequence encoding the polypeptide ended with a termination codon. According to the analysis using the signal sequence prediction software SignalP 4.1, no signal peptide was predicted. In addition, from the sequence homology of motifs, in the polypeptide encoded by the open reading frame AR19M-113, it was predicted that 169 amino acid residues from proline (P) at position 113 to threonine (T) at position 281 were the catalytic domain of the glycoside hydrolase family 12. The already known amino acid sequence which showed the highest sequence identity with the amino acid sequence encoded by the above ORF was that of a GH12 endoglucanase (Genbank: YP_921079.1) of a thermophilic archaeon in the phylum Crenarchaeota, *Thermofilum pendens* strain Hrk 5. Since the homology between the two amino acid sequences that was calculated by the ClustalW algorithm was 35% for the total length and 41% for the GH12 catalytic domain, the aforementioned ORF was verified as a novel sequence.

Figure 1:
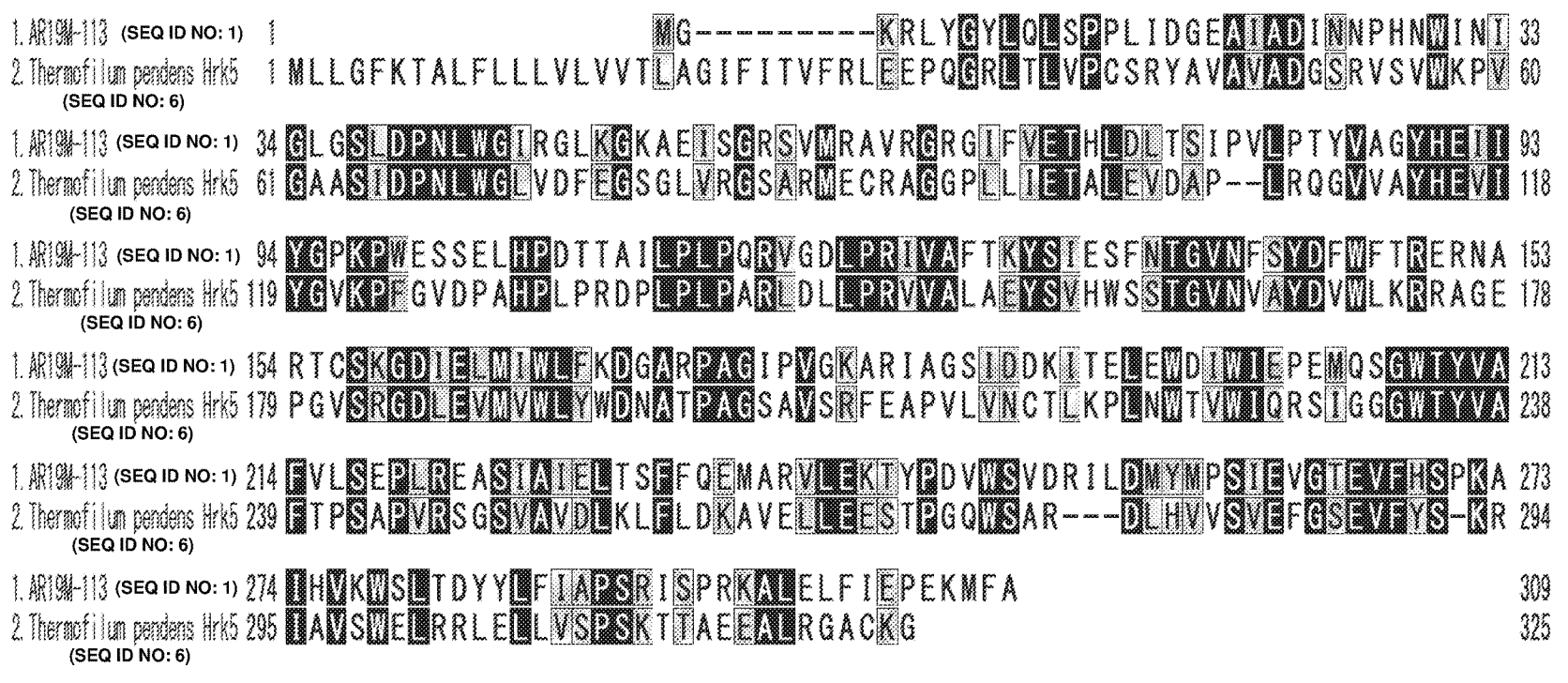

FIG. 1 shows an alignment of the amino acid sequence of the polypeptide (AR19M-113-4) encoded by the open reading frame AR19M-113 and the amino acid sequence (SEQ ID NO: 6) of the GH12 endoglucanase of *Thermofilum pendens* strain Hrk 5. In FIG. 1, the black/white inverted amino acids denote the same amino acid residues (identical) throughout all of these amino acid sequences, the shaded amino acids denote similar amino acid residues (similar) in these amino acid sequences, and the symbols "-" denote deletions (gaps).

<6> Gene Cloning

PCR was conducted using a hot spring soil DNA that had been amplified by the genomic DNA amplification kit (GenomiPhi V2 DNA Amplification Kit, manufactured by GE Healthcare) as a template, and by using a forward primer composed of the nucleotide sequence represented by SEQ ID NO: 5 (5'-CACCATGGGTAAAAGACTCTATGGA-3': 4 nucleotides (CACC) were added to the 5'-end side of the nucleotide sequence represented by SEQ ID NO: 3. The nucleotides CACC added on the 5' side is a sequence for insertion into a vector) and a reverse primer composed of the nucleotide sequence represented by SEQ ID NO: 4 (5'-TCAAGCAAACATTTTTTCTGGTTC-3'). The nucleotide sequence represented by SEQ ID NO: 3 is a nucleotide sequence which is homologous (identical) with a partial sequence including the nucleotides at position 1 to 21 of the nucleotide sequence represented by SEQ ID NO: 2. Moreover, the nucleotide sequence represented by SEQ ID NO: 4 is a nucleotide sequence which is complementary with a partial sequence including the nucleotides at position 907 to 930 of the nucleotide sequence represented by SEQ ID NO: 2. The amplified PCR products were inserted in the pET101/D-TOPO vector of Champion pET Directional TOPO Expression Kits (manufactured by Life Technologies), and transformed into the One Shot TOP10 strain. Positive clones were selected by colony PCR, and then cultured in a LB liquid medium containing 100 mg/L ampicillin at a temperature of 37° C. and 200 rpm for 17 to 20 hours, followed by the preparation of plasmids using the miniprep kit (Wizard plus SV Minipreps DNA Purification System, manufactured by Promega). The prepared plasmids were sequenced by using the 3730 DNA Analyzer sequencer of Life Technologies.

A gene clone AR19M-113-4 was obtained from the open reading frame AR19M-113 by PCR cloning. The nucleotide sequence of AR19M-113-4 which was an endoglucanase candidate gene was completely identical with that of the open reading frame AR19M-113 (SEQ ID NO: 2), and was encoding a polypeptide (AR19M-113-4) composed of 309 amino acid residues (SEQ ID NO: 1).

<7> Gene Expression and Purification of Endoglucanase Enzymatic Protein

After the sequencing, the plasmids having the target gene were introduced in *E. coli* for protein expression by a heat shock method. The BL21 Star (DE3) strain furnished in the Champion pET Directional TOPO Expression Kits (manufactured by Invitrogen) was used as the competent cell for the transformation. *E. coli* having the target gene was inoculated in a LB medium containing 100 mg/L ampicillin and cultured to about OD600=0.2 to 0.8, which was then added with IPTG (isopropyl-β-D(−)-thiogalactopyranoside), and additionally cultured for 5 to 20 hours. By so doing, the expression induction of the target protein was carried out.

After the culture, E. coli was collected by centrifugation, to which 50 mM Tris-HCl buffer (pH8.0) of ⅒-fold volume of the culture liquid was added and suspended. Thereafter, 5 minutes disrupting and 5 minutes halting processes were repeated 7 to 8 times by using an ultrasonic disruption apparatus, Astrason 3000 (manufactured by Misonix, Inc.). By so doing, the crude extract of the gene recombinant E. coli containing the target protein was obtained. The crude extract of the gene recombinant E. coli was filtrated through a filter (pore diameter ϕ=0.45 µm, manufactured by Millipore), and the yielded filtrate was used as a gene recombinant E. coli homogenate supernatant.

The gene recombinant E. coli homogenate supernatant was loaded onto an ion-exchange column HiTrap Q HP (manufactured by GE Healthcare) equilibrated with 50 mM Tris-HCl buffer (pH8.0), by which proteins were fractionated with 0 to 50% concentration gradient with 50 mM Tris-HCl buffer (pH8.0) containing 1M NaCl using a middle-to-high pressure liquid chromatography system AKTA design (manufactured by GE Healthcare). The fractions exhibiting CMC hydrolysis activity were all mixed and then subjected to solution exchange into 50 mM Tris-HCl buffer (pH8.0) containing 750 mM ammonium sulfate using a centrifugal ultrafiltration membrane VIVASPIN 20 (manufactured by Sartorius stedim). The fractions with CMC hydrolysis activity after the solution exchange were loaded onto a hydrophobic interaction separation column HiTrap Phenyl HP (manufactured by GE Healthcare) equilibrated with the same solution, by which proteins were fractionated with 0 to 100% concentration gradient with 50 mM Tris-HCl buffer (pH8.0). The fractions exhibiting CMC hydrolysis activity were all mixed and then concentrated by using the VIVASPIN 20 until the liquid volume reached to about 8 mL. The concentrated sample was added to a gel filtration column Hiload 26/60 superdex 200 pg (manufactured by GE Healthcare) equilibrated with 50 mM Tris-HCl buffer (pH8.0) containing 150 mM NaCl, and fractionated by flowing the same buffer of 1 to 1.5 fold volume of the column volume at a flow rate of 2 to 3 mL/min. The fractions exhibiting CMC hydrolysis activity were all mixed and then subjected to solution exchange into 50 mM Tris-HCl buffer (pH8.0) and concentrated. By so doing, a purified enzyme having the final concentration of about 1 mg/mL was obtained.

The gene recombinant E. coli homogenate supernatant and the purified enzyme were checked by SDS-PAGE analysis (SDS-polyacrylamide gel electrophoresis). The SDS PAGE of the gene recombinant E. coli homogenate supernatant and the purified enzyme was conducted by using the Mini-PROTEAN TGX Stain-Free Gel (manufactured by Bio-Rad Laboratories, Inc.). The electrophoresis samples prepared by respectively mixing the supernatant or the purified enzyme with Tris-SDS βME treatment solution (manufactured by Cosmo Bio Co., Ltd.) at 1:1 were treated at a temperature of 100° C. for 10 minutes. Then, 10 µL of the gene recombinant E. coli homogenate supernatant and 1 µg of the purified enzyme per each sample were respectively electrophoresed.

Figure 2:
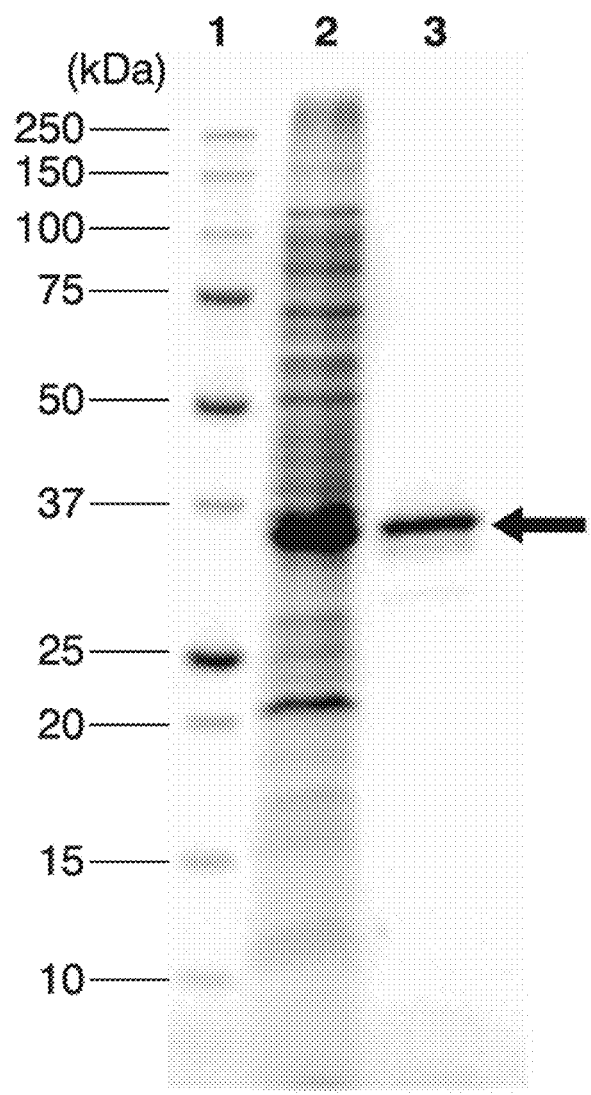
FIG. 2 is a diagram showing the results of SDS-PAGE analysis of the AR19M-113-4 protein obtained by expressing the AR19M-113-4 gene in *E. coli* in Example 1.

FIG. 2 shows the SDS-PAGE analysis result of the gene recombinant E. coli homogenate supernatant prepared from the transformed E. coli introduced with the AR19M-113-4 gene or the purified enzyme which was purified from the gene recombinant E. coli homogenate supernatant. The lane 1 is a molecular weight marker for proteins, and the lanes 2 and 3 show the electrophoresis patterns of the gene recombinant E. coli homogenate supernatant and the purified enzyme, respectively. As a result, in the gene recombinant E. coli homogenate supernatant (lane 2), a strong band was observed near the molecular weight of 35.1 kDa predicted from the amino acid sequence (SEQ ID NO: 1), and in the purified enzyme (lane 3), a single band corresponding with the above band was observed (indicated by an arrow in the figure).

<8> Measurement of Glycoside Hydrolysis Activity (PNPC Hydrolysis Activity) at a Temperature of 90° C. or Less The glycoside hydrolysis activity of the enzymatic protein (AR19M-113-4) encoded by the AR19M-113-4 gene was investigated. In the measurement, a purified enzyme solution prepared by diluting the purified enzyme (concentration of about 1 mg/mL) obtained from the above-mentioned process <7> to 0.02 mg/mL with 50 mM Tris-HCl buffer (pH8.0) was used, and PNPC (manufactured by Sigma-Aldrich Co. LLC.) was used as a substrate.

The measurement of PNPC hydrolysis activity at a temperature of 90° C. or less was carried out by allowing a mixture solution composed of 50 µL of 200 mM acetic acid buffer (pH5.5), 40 µL of purified water, 10 µL of the purified enzyme solution (0.02 mg/mL), and 100 µL of the 4 mM PNPC aqueous solution, to react at a temperature of 30 to 90° C. for 10 minutes. In all the measurements, a mixture solution prepared by adding 50 mM Tris-HCl buffer (pH8.0) in place of the purified enzyme solution and reacting under the same conditions was used as the control lot. Moreover, the substrate solution and the enzyme were respectively and separately kept at retained reaction temperatures for 5 minutes, and then mixed. This timing was set to the initiation of the reaction. In the reaction, every mixture solution was set to a predetermined temperature by using the Eppendorf's Thermomixer. After the completion of the reaction, the same volume of 200 mM aqueous solution of sodium carbonate was added, and the resulting mixture was centrifuged for 5 minutes. By so doing, the supernatant was obtained. The absorbance at 420 µm was measured by using a spectrophotometer, and the amount of p-nitrophenol in the supernatant was calculated by using a calibration curve prepared using p-nitrophenol. The amount of p-nitrophenol produced by the enzymatic hydrolysis was obtained by the difference from the control lot. The enzymatic activity for producing 1 µmol of p-nitrophenol per minute was defined as 1 U, and the value obtained by dividing it by the amount of protein was defined as the specific activity (U/mg).

As a result, it was confirmed that the purified enzyme obtained from the above-mentioned process <7> exhibited hydrolysis activity using PNPC as a substrate at a temperature of 40 to 90° C.

<9> Measurement of Glycoside Hydrolysis Activity (PNPC Hydrolysis Activity) at a Temperature of 95° C. or More The glycoside hydrolysis activity of the enzymatic protein (AR19M-113-4) encoded by the AR19M-113-4 gene was investigated. In the measurement, a purified enzyme solution prepared by diluting the purified enzyme (concentration of about 1 mg/mL) obtained from the above-mentioned process <7> to 0.02 mg/mL with 50 mM Tris-HCl buffer (pH8.0) was used, and PNPC (manufactured by Sigma-Aldrich Co. LLC.) was used as a substrate.

The measurement of PNPC hydrolysis activity at a temperature of 95° C. or higher was carried out by using a glass vial, a rubber stopper, and an aluminum seal (manufactured by Nichiden-Rika Glass Co., Ltd.). Glass vial containers that were coated internally in advance with a 1.5% by mass BSA solution for suppressing the adsorption of enzymatic proteins were used in the reaction. The reaction was carried out by allowing a mixture solution composed of 150 µL of 200 mM acetic acid buffer (pH5.5), 120 μL of purified water, 30 μL of the purified enzyme solution (0.02 mg/mL), and 300 μL of the 4 mM PNPC aqueous solution, to react at a temperature of 95 to 130° C. for 10 minutes. In all the measurements, a mixture solution prepared by adding 50 mM Tris-HCl buffer (pH8.0) in place of the purified enzyme and reacting under the same conditions was used as the control lot. The vial container containing the enzyme solution and fitted with the rubber stopper was kept at retained reaction temperatures for 5 minutes and was then added with a substrate solution which was kept in a separate tube at a temperature of 100° C. for 5 minutes, and the vial and the rubber stopper were immediately sealed using the aluminum seal. This timing was set to the initiation of the reaction. The reaction was carried out by allowing all the mixture solutions to stand for 10 minutes at reaction temperatures using an IKA hot magnetic stirrer. After the completion of the reaction, the amount of p-nitrophenol produced by the enzymatic hydrolysis was obtained and the specific activity (U/mg) was calculated in the same manner as in the above-mentioned process <8>.

As a result, it was confirmed that the purified enzyme obtained from the above-mentioned process <7> exhibited hydrolysis activity using PNPC as a substrate also at a temperature of 95 to 130° C.

<10> Substrate Specificity of AR19M-113-4

The hydrolysis activities for various cellulose substrates and hemicellulose substrates were investigated with the enzymatic protein (AR19M-113-4) encoded by the AR19M-113-4 gene. In the measurement, the purified enzyme solution (0.02 mg/mL) used in the above-mentioned process <8> or <9> was used. In addition, as substrates, PSA, an Avicel powder (fine crystalline cellulose powder, manufactured by Merck), CMC (manufactured by Sigma-Aldrich Co. LLC.), xylan (derived from beechwood, manufactured by Sigma-Aldrich Co. LLC.), xyloglucan (derived from Tamarind, manufactured by Megazyme), laminarin (derived from *Laminaria digitata*, manufactured by Sigma-Aldrich Co. LLC.), lichenan (manufactured by MP Biomedicals, LLC.), β-glucan (derived from barley), PNPG (manufactured by Sigma-Aldrich Co. LLC.), PNPX (manufactured by Sigma-Aldrich Co. LLC.), PNPC (manufactured by Sigma-Aldrich Co. LLC.), and PNPL (manufactured by Sigma-Aldrich Co. LLC.) were used.

PSA was prepared by once dissolving an Avicel powder (fine crystalline cellulose powder, manufactured by Merck) with a phosphoric acid solution, then precipitating it by adding sterile purified water, and thereafter washing the same until the pH reached 5 or higher. It should be noted that PSA used for all the following experiments was prepared by the above method.

More specifically, the enzymatic reaction was carried out by first preincubating a mixture solution composed of 50 μL of 200 mM acetic acid buffer (pH5.5), 10 μL of the purified enzyme solution (0.02 mg/mL) and 40 μL of purified water as a reaction solution at a temperature of 70° C. or 90° C. for 5 minutes, then additionally adding 100 μL of each substrate solution (1% by mass aqueous solutions of PSA, Avicel powder, CMC, xylan, xyloglucan, β-glucan, lichenan and laminarin, and 4 mM aqueous solutions of PNPG, PNPX, PNPC and PNPL) which was kept at the same temperature thereto, and incubating the resulting mixture solution at a temperature of 70° C. or 90° C. for 10 minutes. In the reaction, the mixture solution was stirred by applying vibration of 1,400 rpm using the Thermomixer (manufactured by Eppendorf) so as to avoid the precipitation of insoluble substrates. In all the measurements, a mixture solution prepared by adding 50 mM Tris-HCl buffer (pH8.0) in place of the purified enzyme solution and reacting under the same conditions was used as the control lot.

After the completion of the reaction, in the reaction where PNPG, PNPX, PNPC or PNPL was used as the substrate, as in the case of investigating the PNPC hydrolysis activity of AR19M-113-4 of the above-mentioned process <8>, the absorbance at 420 μm of the supernatant of the mixture solution after the reaction was measured, the amount of p-nitrophenol produced by the hydrolysis was obtained, and the specific activity (U/mg) was calculated. In the reaction where PSA, Avicel powder, CMC, xylan, xyloglucan, β-glucan, lichenan or laminarin was used as a substrate, after the completion of the reaction, the same volume of a 3,5-dinitrosalicylic acid reagent (DNS solution) was added. The resulting mixture was treated by heating at a temperature of 100° C. for 5 minutes, cooled down on ice for 5 minutes, and then centrifuged at 17,400 g for 5 minutes. By so doing, the supernatant was obtained. The absorbance at 540 μm was measured by using a spectrophotometer, and the amount of reduced sugar in the supernatant was calculated by using a calibration curve prepared with glucose. The amount of reduced sugar produced by the enzymatic hydrolysis was obtained by the difference from the control lot. However, the amount of reduced sugar produced by the hydrolysis of xylan was obtained by using a calibration curve prepared with xylan. The enzymatic activity for producing 1 μmol of reduced sugar per minute defined as 1 U, and the value obtained by dividing it by the amount of protein was defined as the specific activity (U/mg).

Figure 3:
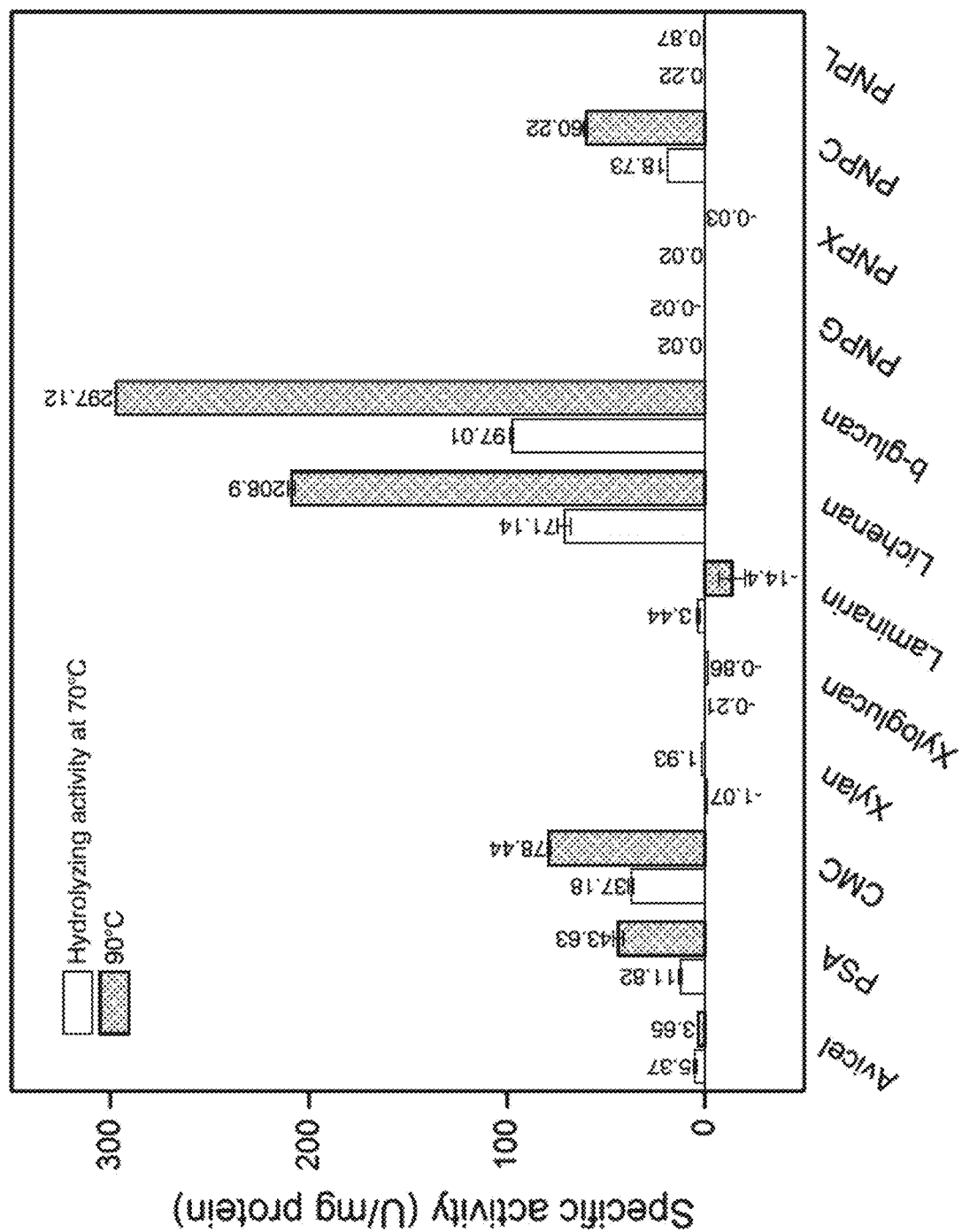
FIG. 3 is a diagram showing the measurement results of the hydrolytic activity of the AR19M-113-4 protein expressed in *E. coli* in Example 1 for each substrate.

Each measurement was performed by three independent experiments, from which the mean value and the standard errors were obtained. The measurement results are shown in FIG. 3. As a result, AR19M-113-4 exhibited a particularly high hydrolysis activity for lichenan and β-glucan (297.12 U/mg and 208.9 U/mg, respectively at a temperature of 90° C.), exhibited a high degradation activity also for CMC and PNPC (78.44 U/mg and 60.22 U/mg, respectively at a temperature of 90° C.), and exhibited a hydrolysis activity also for PSA (43.63 U/mg). On the other hand, it exhibited almost no degradation activity for other substrates. In addition, with respect to all the substrates for which hydrolysis activity was exhibited, higher degradation activity was observed at 90° C. than at 70° C. From these results described above, AR19M-113-4 was shown to be a hyperthermostable endoglucanase with particularly high specificity for substrates composed of β-1,3-linked- and β-1,4-linked glucans.

<11> Temperature Dependency of Hydrolysis Activity Using PNPC and β-Glucan as Substrates The temperature dependency of the glycoside hydrolysis activity of the enzymatic protein (AR19M-113-4) encoded by the AR19M-113-4 gene was investigated. In the measurement, a purified enzyme solution prepared by diluting the purified enzyme (concentration of about 1 mg/mL) obtained from the above-mentioned process <7> to 0.02 mg/mL with 50 mM Tris-HCl buffer (pH8.0) was used. In addition, since the difference in temperature characteristics among the known endoglucanases depending on the substrate had been reported, PNPC and β-glucan derived from barley (manufactured by Sigma-Aldrich Co. LLC.) with which the highest activity was observed in the substrate specificity analysis were used as substrates.

The measurement of the temperature dependency of the PNPC hydrolysis activity of the purified AR19M-113-4 was conducted in the same manner as in the above-mentioned process <8> when the reaction temperature was set to 30, 40, 50, 60, 70, 80, 85, or 90° C., wherein the amount of p-nitrophenol produced by the hydrolysis was obtained, and the specific activity (U/mg) was calculated.

In addition, the measurement was conducted in the same manner as in the above-mentioned process <9> when the reaction temperature was set to 95, 100, 105, 110, 115, 120, 125, or 130° C., wherein the amount of p-nitrophenol produced by the hydrolysis was obtained, and the specific activity (U/mg) was calculated.

The measurement of the temperature dependency of the β-glucan hydrolysis activity of the purified AR19M-113-4 was conducted in the same manner as in the above-mentioned process <8> to perform the enzymatic reaction, with the exception that 200 mM acetic acid buffer (pH4.5) and a 1% by mass β-glucan aqueous solution serving as a substrate were used, when the reaction temperature was set to 30, 40, 50, 60, 70, 80, 85, or 90° C., wherein the amount of reduced sugar produced by the hydrolysis was obtained and the specific activity (U/mg) was calculated in the same manner as in the above-mentioned process <10>.

In addition, the enzymatic reaction was carried out in the same manner as in the above-mentioned process <9>, with the exception that 200 mM acetic acid buffer (pH4.5) and a 1% by mass β-glucan aqueous solution serving as a substrate were used, when the reaction temperature was set to 95, 100, 105, 110, 115, or 120° C., wherein the amount of reduced sugar produced by the hydrolysis was obtained and the specific activity (U/mg) was calculated in the same manner as in the above-mentioned process <10>.

Figure 4:
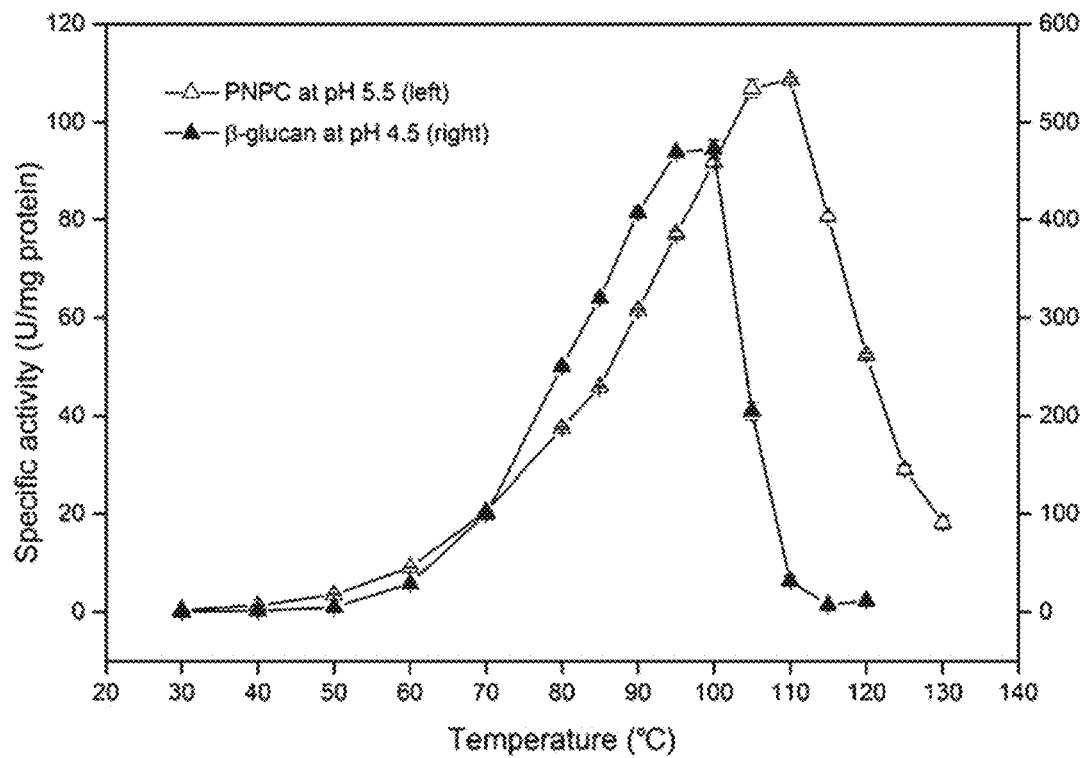
FIG. 4 is a diagram showing the results of measuring the glycoside hydrolysis activity of the AR19M-113-4 protein expressed in *E. coli* when PNPC was used as a substrate (pH5.5) and when β-glucan was used as a substrate (pH4.5) at respective temperatures in Example 1. The left vertical axis represents the scale of the PNPC hydrolysis activity, and the right vertical axis represents the scale of the β-glucan hydrolysis activity.

Each measurement was performed by three independent experiments, from which the mean value and the standard errors were obtained. The measurement results are shown in FIG. 4. FIG. 4 is a diagram showing the results of measuring the glycoside hydrolysis activity of the purified enzyme AR19M-113-4 when PNPC was used as a substrate (pH5.5) and when β-glucan was used as a substrate (pH4.5) at respective temperatures, wherein the horizontal axis represents the temperature. In FIG. 4, the left vertical axis represents the scale of the PNPC hydrolysis activity, and the right vertical axis represents the scale of the β-glucan hydrolysis activity.

AR19M-113-4 exhibited PNPC hydrolysis activity in a temperature range from 40 to 130° C. at a pH of 5.5, and the optimum temperature (Topt) showing the highest activity was 110° C. at a pH of 5.5.

In addition, for the β-glucan substrate, it exhibited the hydrolysis activity in a temperature range from 40 to 120° C. at a pH of 4.5, and the optimum temperature (Topt) showing the highest activity was 100° C. at a pH of 4.5. From these results described above, the AR19M-113-4 endoglucanase was confirmed to exhibit different temperature characteristics depending on the substrate, although the optimum temperature was 100° C. or higher in both cases.

<12> pH Dependency of Hydrolysis Activity Using PNPC and β-Glucan as Substrates

The pH dependency of the glycoside hydrolysis activity of the enzymatic protein (AR19M-113-4) encoded by the AR19M-113-4 gene was investigated. In the measurement, a purified enzyme solution prepared by diluting the purified enzyme (concentration of about 1 mg/mL) obtained from the above-mentioned process <7> to 0.02 mg/mL with 50 mM Tris-HCl buffer (pH8.0) was used. In addition, PNPC and β-glucan derived from barley (manufactured by Sigma-Aldrich Co. LLC.) were used as substrates.

The measurement of the pH dependency of the PNPC hydrolysis activity of the purified AR19M-346-18 was conducted in the same manner as in the above-mentioned process <8>, except for reacting a mixture solution composed of 50 μL of McIlvaine buffer (pH3 to 8), 40 μL of purified water, 10 μL of the purified enzyme solution (0.02 mg/mL) and 100 μL of the 4 mM PNPC aqueous solution, at a temperature of 90° C. for 10 minutes, wherein the amount of p-nitrophenol produced by the enzymatic hydrolysis was obtained, and the PNPC hydrolysis activity (U/mg) was calculated.

Similarly, for the β-glucan hydrolysis activity, enzymatic reaction was carried out in the same manner as in the above-mentioned process <8>, except for reacting a mixture solution composed of 50 μL of McIlvaine buffer (pH3 to 8), 40 μL of purified water, 10 μL of the purified enzyme solution (0.02 mg/mL) and 100 μL of a 1% by mass β-glucan aqueous solution, at a temperature of 90° C. for 10 minutes, wherein the amount of reduced sugar produced by the hydrolysis was obtained and the β-glucan hydrolysis activity (U/mg) was calculated in the same manner as in the above-mentioned process <10>.

Figure 5:
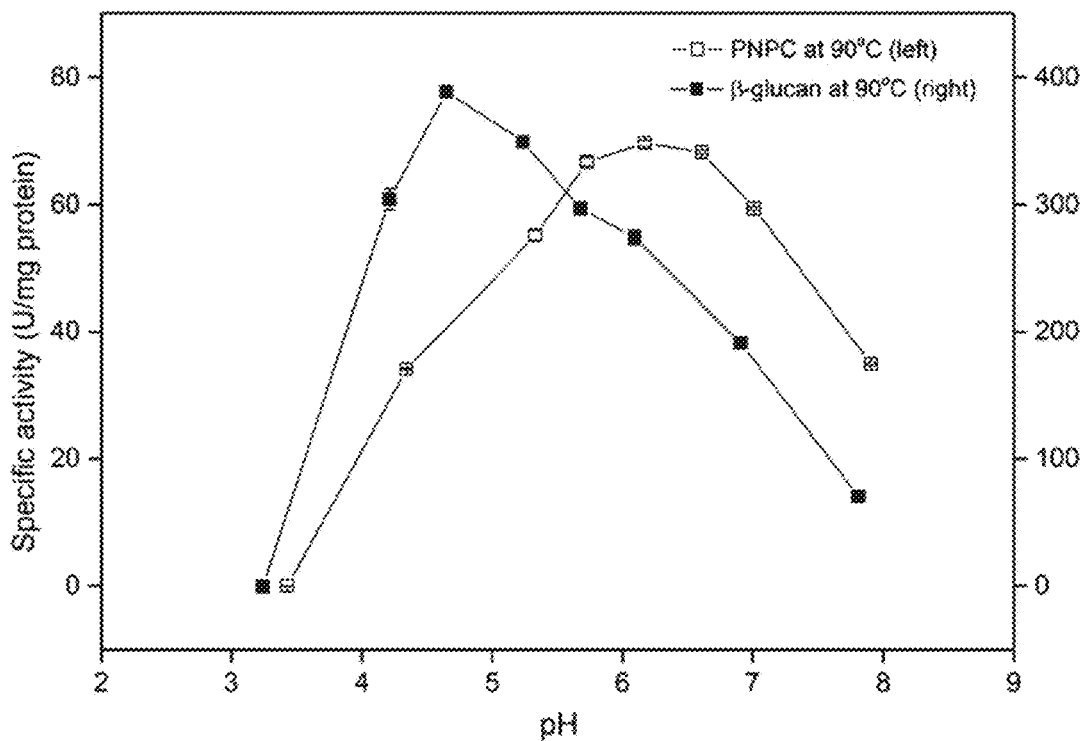
FIG. 5 is a diagram showing the results of measuring the glycoside hydrolysis activity (90° C.) of the AR19M-113-4 protein expressed in *E. coli* when PNPC was used as a substrate and when β-glucan was used as a substrate at respective pH values in Example 1. The left vertical axis represents the scale of the PNPC hydrolysis activity, and the right vertical axis represents the scale of the β-glucan hydrolysis activity.

Each measurement was performed by three independent experiments, from which the mean value and the standard errors were obtained. The measurement results are shown in FIG. 5. FIG. 5 is a diagram showing the results of measuring the glycoside hydrolysis activity (90° C.) of the purified enzyme AR19M-113-4 when PNPC was used as a substrate and when β-glucan was used as a substrate at respective pH values, wherein the horizontal axis represents the pH. In FIG. 5, the left vertical axis represents the scale of the PNPC hydrolytic activity, and the right vertical axis represents the scale of the β-glucan hydrolysis activity. The pH was plotted by the actual measurement values of the mixture solution containing the substrate, the buffer, and the enzyme.

AR19M-113-4 exhibited PNPC hydrolysis activity within a pH range of 4 to 8 at a temperature of 90° C., and the optimum pH was around a pH of 5.5 to 6.5 at a temperature of 90° C. (the actual measurement value of the mixture solution containing the substrate, the buffer, and the enzyme was from pH5.73 to 6.71). In addition, in the case of using the β-glucan substrate, although hydrolysis activity was exhibited in the same manner within a pH range of 4 to 8 at a temperature of 90° C., the optimum pH was a pH of 4.5 (the actual measurement value of the mixture solution containing the substrate, the buffer, and the enzyme was a pH of 4.65) at a temperature of 90° C.

<13> Thermal Stability of AR19M-113-4

In order to investigate the thermal stability (heat resistance) of AR19M-113-4, preincubation was conducted for 1 hour to 40 hours, and the PNPC hydrolysis activity of the enzymatic protein was measured at respective temperatures.

In the measurement, the purified enzyme solution (0.02 mg/mL) used in the above-mentioned process <8> or <9> was used. The preincubation of each purified enzyme solution was carried out by keeping the temperature of a mixture solution (pH5.5) composed of 10 μL of the purified enzyme, 40 μL of purified water, and 50 μL of a 200 mM acetic acid buffer, at respective temperature of 80 to 99° C. for 0, 1, 2, 4, 8, 16, 24, or 40 hours. The measurement of the PNPC hydrolysis activity of the purified enzyme was conducted in the same manner as in the above-mentioned process <8>, except for separately heating the preincubated mixture solution and a 4 mM PNPC aqueous solution respectively at a temperature of 90° C. for 5 minutes, then adding the same amount of the PNPC aqueous solution to the mixture solution, and reacting the resulting mixture for 10 minutes at a temperature of 90° C. The amount of p-nitrophenol produced by the enzymatic hydrolysis was obtained, and the PNPC hydrolysis activity (U/mg) was calculated.

Figure 6:
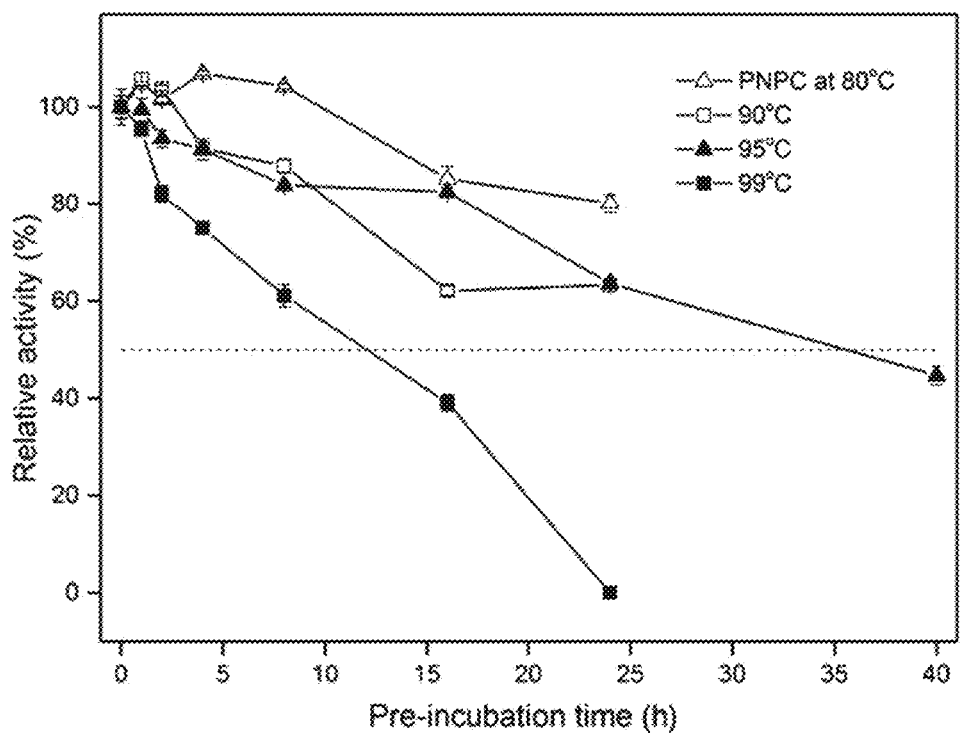
FIG. 6 is a diagram showing the measurement results of the thermal stability (heat resistance) of the AR19M-113-4 protein expressed in *E. coli* in Example 1 for each substrate.

The measurement results are shown in FIG. 6. The enzymatic activity was shown as the relative value (Relative activity, %) assuming that the activity of the nontreated lot (without preincubation) was 100%. The preincubation time at which the enzymatic activity was reduced to 50% of that of the nontreated lot was set to the half-life $T_{half}$. When the preincubation temperature was from 80 to 90° C., AR19M-113-4 did not lose the PNPC hydrolysis activity within the measurement time, and the half-life $T_{half}$ was 24 hours or longer. The half-life $T_{half}$ was about 40 hours at a temperature of 95° C. and 12 to 13 hours at a temperature of 99° C., respectively.

<14> Measurement of Thermal Degradation Temperature $T_m$ (Melting Temperature)

As an indicator associated with the thermal stability of a protein, thermal denaturation temperature or thermal degradation temperature, $T_m$ (melting temperature) is often used. The preincubation temperature at which the enzymatic activity is reduced to 50% of that of the nontreated lot by preliminary heating (preincubation) for a certain time is substantially equal to the thermal degradation temperature $T_m$ of the protein, and can be obtained by measuring the enzymatic activity. The thermal degradation temperature $T_m$ of AR19M-113-4 was obtained by this method.

More specifically, by using a temperature $T_{50}$, at which the PNPC hydrolysis activity is reduced to 50%, as an indicator by preliminary heating for 30 minutes under substrate-free conditions, the thermal stability of AR19M-113-4 was investigated. Each data was subjected to an approximation using a logistic function, and the temperature at which the approximation curve reached the relative activity value of 50% was defined as $T_{50}$.

In the measurement, the purified enzyme solution (0.02 mg/mL) used in the above-mentioned process <8> or <9> was used. The preincubation of each purified enzyme solution was carried out by keeping the temperature of a mixture solution (pH5.5) composed of 10 µL of the purified enzyme solution, 40 µL of purified water, and 50 µL of a 200 mM acetic acid buffer, at respective temperature of 80 to 130° C. for 30 minutes. The measurement of the PNPC hydrolysis activity was conducted in the same manner as in the above-mentioned process <8>, except for separately heating the preincubated mixture solution and a 4 mM PNPC aqueous solution respectively at a temperature of 90° C. for 5 minutes, then adding the same amount of the mixture solution and the PNPC aqueous solution, and reacting the resulting mixture for 10 minutes at a temperature of 90° C. The amount of p-nitrophenol yielded by the enzymatic hydrolysis was obtained, and the PNPC hydrolysis activity (U/mg) was calculated.

The measurement results are shown in FIG. 7. The enzymatic activity was shown as the relative value (Relative activity, %) assuming that the activity of the nontreated lot (without preincubation) was 100%. AR19M-113-4 had a $T_{50}$ of 104.4° C.

SEQUENCE LISTING

```
<160> NUMBER OF SEQ ID NOS: 6

<210> SEQ ID NO 1
<211> LENGTH: 309
<212> TYPE: PRT
<213> ORGANISM: Unknown
<220> FEATURE:
<223> OTHER INFORMATION: Amino Acid sequence of AR19M-113-4; obtained
      from a microorganism living in high temperature hot spring soils;
      has homology with an amino acid sequence of endoglucanase of a
      thermophilic archaeon in phylum Crenarchaeota, Thermofilum pendens
      strain Hrk 5

<400> SEQUENCE: 1

Met Gly Lys Arg Leu Tyr Gly Tyr Leu Gln Leu Ser Pro Pro Leu Ile
1               5                   10                  15

Asp Gly Glu Ala Ile Ala Asp Ile Asn Asn Pro His Asn Trp Ile Asn
            20                  25                  30

Ile Gly Leu Gly Ser Leu Asp Pro Asn Leu Trp Gly Ile Arg Gly Leu
        35                  40                  45

Lys Gly Lys Ala Glu Ile Ser Gly Arg Ser Val Met Arg Ala Val Arg
    50                  55                  60

Gly Arg Gly Ile Phe Val Glu Thr His Leu Asp Leu Thr Ser Ile Pro
65                  70                  75                  80

Val Leu Pro Thr Tyr Val Ala Gly Tyr His Glu Ile Ile Tyr Gly Pro
                85                  90                  95

Lys Pro Trp Glu Ser Ser Glu Leu His Pro Asp Thr Thr Ala Ile Leu
            100                 105                 110

Pro Leu Pro Gln Arg Val Gly Asp Leu Pro Arg Ile Val Ala Phe Thr
        115                 120                 125

Lys Tyr Ser Ile Glu Ser Phe Asn Thr Gly Val Asn Phe Ser Tyr Asp
    130                 135                 140
```

```
Phe Trp Phe Thr Arg Glu Arg Asn Ala Arg Thr Cys Ser Lys Gly Asp
145                 150                 155                 160

Ile Glu Leu Met Ile Trp Leu Phe Lys Asp Gly Ala Arg Pro Ala Gly
                165                 170                 175

Ile Pro Val Gly Lys Ala Arg Ile Ala Gly Ser Ile Asp Asp Lys Ile
            180                 185                 190

Thr Glu Leu Glu Trp Asp Ile Trp Ile Glu Pro Glu Met Gln Ser Gly
        195                 200                 205

Trp Thr Tyr Val Ala Phe Val Leu Ser Glu Pro Leu Arg Glu Ala Ser
    210                 215                 220

Ile Ala Ile Glu Leu Thr Ser Phe Phe Gln Glu Met Ala Arg Val Leu
225                 230                 235                 240

Glu Lys Thr Tyr Pro Asp Val Trp Ser Val Asp Arg Ile Leu Asp Met
                245                 250                 255

Tyr Met Pro Ser Ile Glu Val Gly Thr Glu Val Phe His Ser Pro Lys
            260                 265                 270

Ala Ile His Val Lys Trp Ser Leu Thr Asp Tyr Tyr Leu Phe Ile Ala
        275                 280                 285

Pro Ser Arg Ile Ser Pro Arg Lys Ala Leu Glu Leu Phe Ile Glu Pro
    290                 295                 300

Glu Lys Met Phe Ala
305

<210> SEQ ID NO 2
<211> LENGTH: 930
<212> TYPE: DNA
<213> ORGANISM: Unknown
<220> FEATURE:
<223> OTHER INFORMATION: Open reading frame AR19M-113; nucleotide
      sequence of AR19M-113-4; obtained from a microorganism which lives
      in high temperature hot spring soils; present in natural

<400> SEQUENCE: 2
atgggtaaaa gactctatgg atatttacag ctgtcgcctc cgttaattga cggagaggct      60
attgcagata ttaataatcc gcataactgg atcaatattg ggttgggcag tttagatcct     120
aatctatggg gtatcagagg tctcaagggt aaggcggaga taagtggaag gtctgtgatg     180
agggctgtta gaggaagggg catatttgtt gagacgcatc ttgatctaac cagtatacca     240
gtgttaccaa catatgtagc aggctatcac gagatcatat atggtcctaa ccatgggag      300 agctcggagc tgcatccaga taccacagct attttgccat tacctcagag agtaggtgat     360
ttacccagga tagtggcttt cacgaaatac tctatagaga gcttcaatac aggtgtcaac     420
ttctcatatg atttctggtt tactagagag cgcaatgcga aacatgttc aaagggagac     480 atagagctga tgatatggct attcaaagat ggggcacggc cagcaggtat acctgttggg     540
aaagcgagga tagctgggtc catcgatgat aagataactg agctggaatg ggatatatgg     600
atagagcctg agatgcaaag cggatggacc tatgttgcct ttgtgcttag cgagccattg     660
agagaagcct cgattgctat agagcttaca tcgttttttcc aagaaatggc gagggtattg     720
gagaagacat accctgatgt gtggagtgtc gatagaatcc tagatatgta tatgccttct     780
attgaggtgg gcactgaggt tttccactcg ccaaaggcta tacatgtgaa atggagcttg     840
acagattatt atctgtttat agcaccttct aggataagcc ctagaaaggc tcttgaacta     900
tttatagaac cagaaaaaat gtttgcttga                                      930

<210> SEQ ID NO 3
```

```
<211> LENGTH: 21
<212> TYPE: DNA
<213> ORGANISM: Artificial Sequence
<220> FEATURE:
<223> OTHER INFORMATION: Primer; a nucleotide sequence which is
      homologous (identical) with a partial sequence including the
      nucleotides at position 1 to 21 of the nucleotide sequence of SEQ
      ID NO: 2; artificially synthesized

<400> SEQUENCE: 3
atgggtaaaa gactctatgg a                                              21

<210> SEQ ID NO 4
<211> LENGTH: 24
<212> TYPE: DNA
<213> ORGANISM: Artificial Sequence
<220> FEATURE:
<223> OTHER INFORMATION: Primer; reverse primer which is complementary
      with a partial sequence including the nucleotides at position 907
      to 930 of the nucleotide sequence of SEQ ID NO:2; primer for gene
      cloning; artificially synthesized

<400> SEQUENCE: 4
tcaagcaaac atttttctg gttc                                            24

<210> SEQ ID NO 5
<211> LENGTH: 25
<212> TYPE: DNA
<213> ORGANISM: Artificial Sequence
<220> FEATURE:
<223> OTHER INFORMATION: Primer; forward primer in which 4 nucleotides
      (CACC) are added to the 5'-end side of the nucleotide sequence of
      SEQ ID NO:3; primer for gene cloning; artificially synthesized

<400> SEQUENCE: 5
caccatgggt aaaagactct atgga                                          25

<210> SEQ ID NO 6
<211> LENGTH: 325
<212> TYPE: PRT
<213> ORGANISM: Unknown
<220> FEATURE:
<223> OTHER INFORMATION: Thermofilum pendens str. Hrk 5; GH12
      endoglucanase

<400> SEQUENCE: 6

Met Leu Leu Gly Phe Lys Thr Ala Leu Phe Leu Leu Val Leu Val
1               5                   10                  15

Val Thr Leu Ala Gly Ile Phe Ile Thr Val Phe Arg Leu Glu Glu Pro
            20                  25                  30

Gln Gly Arg Leu Thr Leu Val Pro Cys Ser Arg Tyr Ala Val Ala Val
        35                  40                  45

Ala Asp Gly Ser Arg Val Ser Val Trp Lys Pro Val Gly Ala Ala Ser
    50                  55                  60

Ile Asp Pro Asn Leu Trp Gly Leu Val Asp Phe Glu Gly Ser Gly Leu
65                  70                  75                  80

Val Arg Gly Ser Ala Arg Met Glu Cys Arg Ala Gly Gly Pro Leu Leu
                85                  90                  95

Ile Glu Thr Ala Leu Glu Val Asp Ala Pro Leu Arg Gln Gly Val Val
            100                 105                 110

Ala Tyr His Glu Val Ile Tyr Gly Val Lys Pro Phe Gly Val Asp Pro
        115                 120                 125

Ala His Pro Leu Pro Arg Asp Pro Leu Pro Leu Pro Ala Arg Leu Asp
    130                 135                 140
```

-continued

```
Leu Leu Pro Arg Val Val Ala Leu Ala Glu Tyr Ser Val His Trp Ser
145                 150                 155                 160

Ser Thr Gly Val Asn Val Ala Tyr Asp Val Trp Leu Lys Arg Arg Ala
            165                 170                 175

Gly Glu Pro Gly Val Ser Arg Gly Asp Leu Glu Val Met Val Trp Leu
            180                 185                 190

Tyr Trp Asp Asn Ala Thr Pro Ala Gly Ser Ala Val Ser Arg Phe Glu
        195                 200                 205

Ala Pro Val Leu Val Asn Cys Thr Leu Lys Pro Leu Asn Trp Thr Val
        210                 215                 220

Trp Ile Gln Arg Ser Ile Gly Gly Gly Trp Thr Tyr Val Ala Phe Thr
225                 230                 235                 240

Pro Ser Ala Pro Val Arg Ser Gly Ser Val Ala Val Asp Leu Lys Leu
            245                 250                 255

Phe Leu Asp Lys Ala Val Glu Leu Leu Glu Glu Ser Thr Pro Gly Gln
            260                 265                 270

Trp Ser Ala Arg Asp Leu His Val Val Ser Val Glu Phe Gly Ser Glu
            275                 280                 285

Val Phe Tyr Ser Lys Arg Ile Ala Val Ser Trp Glu Leu Arg Arg Leu
        290                 295                 300

Glu Leu Leu Val Ser Pro Ser Lys Thr Thr Ala Glu Glu Ala Leu Arg
305                 310                 315                 320

Gly Ala Cys Lys Gly
                325
```

What is claimed is:

1. An isolated recombinant hyperthermostable endoglucanase comprising
   a polypeptide consisting of the amino acid sequence set forth in SEQ ID NO: 1; and
   at least one region selected from the group consisting of a cellulose-binding module, linker domain, a signal peptide and a tag.

2. An isolated recombinant polynucleotide comprising
   a nucleotide sequence that encodes the polypeptide consisting of the amino acid sequence set forth in SEQ ID NO: 1 and
   a nucleotide sequence that encodes at least one region selected from the group consisting of a cellulose-binding module, a linker sequence, a signal peptide and a tag.

3. An expression vector, which is incorporated with the polynucleotide according to claim 2, and
   which is able to express a polypeptide having glycoside hydrolysis activity in a host cell.

4. A transformant, which is introduced with the expression vector according to claim 3.

5. The transformant according to claim 4, which is a eukaryotic microbe.

6. A method for producing a hyperthermostable endoglucanase, the method comprising producing a hyperthermostable endoglucanase in the transformant according to claim 4 by culturing the transformant.

7. A glycoside hydrolase mixture, comprising the hyperthermostable endoglucanase according to claim 1 and at least one of other glycoside hydrolases.

8. A glycoside hydrolase mixture, comprising a hyperthermostable endoglucanase encoded by the polynucleotide according to claim 2 and at least one of other glycoside hydrolases.

9. A glycoside hydrolase mixture, comprising a hyperthermostable endoglucanase produced by the method for producing a hyperthermostable endoglucanase according to claim 6 and at least one of other glycoside hydrolases.

10. A method for producing a lignocellulose degradation product, the method comprising producing a lignocellulose degradation product by bringing a material composed of lignocellulose comprising cellulose into contact with the hyperthermostable endoglucanase according to claim 1.

11. A method for producing a lignocellulose degradation product, the method comprising producing a lignocellulose degradation product by bringing a material composed of lignocellulose comprising cellulose into contact with a hyperthermostable endoglucanase encoded by the polynucleotide according to claim 2.

12. A method for producing a lignocellulose degradation product, the method comprising producing a lignocellulose degradation product by bringing a material composed of lignocellulose comprising cellulose into contact with the transformant according to claim 4.

13. A method for producing a lignocellulose degradation product, the method comprising producing a lignocellulose degradation product by bringing a material composed of lignocellulose comprising cellulose into contact with a hyperthermostable endoglucanase produced by the method for producing a hyperthermostable endoglucanase according to claim 6.

14. A method for producing a lignocellulose degradation product, the method comprising producing a lignocellulose degradation product by bringing a material composed of lignocellulose comprising cellulose into contact with the glycoside hydrolase mixture according to claim 7.

15. A method for producing a lignocellulose degradation product, the method comprising producing a lignocellulose degradation product by bringing a material composed of lignocellulose comprising cellulose into contact with the glycoside hydrolase mixture according to claim 8.

16. A method for producing a lignocellulose degradation product, the method comprising producing a lignocellulose degradation product by bringing a material composed of lignocellulose comprising cellulose into contact with the glycoside hydrolase mixture according to claim 9.

\* \* \* \* \*